US009981974B2

(12) United States Patent
Wang et al.

(10) Patent No.: US 9,981,974 B2
(45) Date of Patent: May 29, 2018

(54) SMALL MOLECULES TARGETING ANDROGEN RECEPTOR NUCLEAR LOCALIZATION AND/OR LEVEL IN PROSTATE CANCER

(71) Applicant: University of Pittsburgh—Of the Commonwealth System of Higher Education, Pittsburgh, PA (US)

(72) Inventors: Zhou Wang, Pittsburgh, PA (US); Joel Byron Nelson, Pittsburgh, PA (US); Minh Bao Nguyen, Pittsburgh, PA (US); John S. Lazo, Pittsburgh, PA (US); Paul A. Johnston, Pittsburgh, PA (US); Peter Wipf, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days. days.

(21) Appl. No.: 15/457,774

(22) Filed: Mar. 13, 2017

(65) Prior Publication Data

US 2017/0247382 A1    Aug. 31, 2017

Related U.S. Application Data

(62) Division of application No. 14/351,126, filed as application No. PCT/US2012/059558 on Oct. 10, 2012.

(60) Provisional application No. 61/546,215, filed on Oct. 12, 2011.

(51) Int. Cl.
*C07D 487/04* (2006.01)
*C07D 471/08* (2006.01)

(52) U.S. Cl.
CPC ......... *C07D 487/04* (2013.01); *C07D 471/08* (2013.01)

(58) Field of Classification Search
None
See application file for complete search history.

(56) References Cited

U.S. PATENT DOCUMENTS

| | | | |
|---|---|---|---|
| 4,186,205 A | 1/1980 | Bender | |
| 5,145,858 A * | 9/1992 | Adams | C07D 207/22 514/300 |
| 5,317,019 A | 5/1994 | Bender et al. | |
| 6,680,342 B2 | 1/2004 | Young et al. | |
| 2002/0022630 A1 | 2/2002 | Zhang et al. | |
| 2008/0009506 A1* | 1/2008 | Kusama | C07D 233/64 514/255.05 |
| 2009/0163545 A1 | 6/2009 | Goldfarb | |
| 2011/0003839 A1 | 1/2011 | Jung et al. | |

FOREIGN PATENT DOCUMENTS

| | | |
|---|---|---|
| EP | 1992618 | 11/2008 |
| WO | WO 2001/029038 | 4/2001 |
| WO | WO 2006/030977 | 3/2006 |
| WO | WO 2006/044504 | 4/2006 |
| WO | WO 2007/002701 | 1/2007 |
| WO | WO 2008/011130 | 1/2008 |
| WO | WO 2011/050353 | 4/2011 |

OTHER PUBLICATIONS

Gallagher et al., C-7 Functionalization of 6,7-dihydro[5H]pyrrolo[1,2-a]imidazoles: Activation Via Quaternization With MEMCI, 1989, Tetrahedron Letters, vol. 30, No. 48, 6599-6602.*
Ai et al., "HDAC6 Regulates Androgen Receptor Hypersensitivity and Nuclear Localization via Modulating Hsp90 Acetylation in Castration-resistant Prostate Cancer," *Mol. Endocrinol.*, 23(12): 1963-1972, 2009.
Bravo-Altamirano et al. "Synthesis and Structure—Activity Relationships of Benzothienothiazepinone Inhibitors of Protein Kinase D," *ACS Med. Chem. Lett.*, 2:154-159, 2011.
Clausen et al. "In Vitro Cytoxicity and In Vivo Efficacy, Pharmacokinetics, and Metabolism of 10074-G5, a Novel Small-MoleculeInhibitor of c-Myc/Max Dimerization," *The Journal of Pharmacology and Experimental Therapeutics*, 335(3): 715-727, 2010.

(Continued)

*Primary Examiner* — Kristin A Vajda
(74) *Attorney, Agent, or Firm* — Klarquist Sparkman, LLP

(57) ABSTRACT

A method for treating prostate cancer in a subject, comprising administering a therapeutically effective amount of at least one agent to the subject, wherein the agent is selected from:
(a) a phenyl-substituted imidazole, or a pharmaceutically acceptable salt or ester thereof; or
(b) a compound, or a pharmaceutically acceptable salt or ester thereof, having a formula I of:

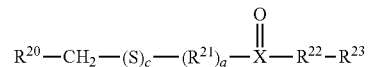

wherein $R^{20}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;
$R^{21}$ is an alkanediyl or a substituted alkanediyl;
a is 0 or 1;
c is 0 or 1;
X is C or S;
$R^{22}$ is a moiety that includes at least one divalent amino radical; and
$R^{23}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group.

21 Claims, 16 Drawing Sheets

(56) References Cited

OTHER PUBLICATIONS

Claxton et al., "Cyclization of Lactamimide Ketones to Imidazo[1,2-a]-azacycloalkanes with Hypoglycemic Activity", *Journal of Medicinal Chemistry*, 17(3): 364-367, 1974.
Demchenko et al, "Synthesis and antimycotic activity of 3-aryl-6,7-dihydro-5H-pyrrolo[1,2-a imidazoles", *Khimiko-Farmatsevticheskii Zhurnal.*, 21(11): 1335-1338, 1987.
Frantz et al. "Large-Scale asymmetric Synthesis of the Bioprotective Agent JP4-039 and Analogs," *Organic Letters*, 2011.
Frutos et al. "Expedient synthesis of substituted imidazoles from nitriles," *Tetrahedrom Letters*, 46: 8369-8372, 2005.
Graczyk et al., "The neuroprotective action of JNK3 inhibitors based on the , 7-dihydro-5H-pyrrolo[1,2-α]imidazole scaffold," *Bioorganic & Medical Chemistry Letters*, 15: 4666-4670, 2005.
Kovtunenko et al, "Derivatives of 2a,4a-diazacyclopent[c,d]azulene", *Khimiya Geterotsiklicheskikh Soedinenii.*, 8: 1072-1077, 1996.
Kovtunenko et al., "Derrivatives of 1,2-tetramethyleneimidazole", *Ukrainskii Khimicheskii Zhurna (Russian Edition)*, 62(3-4): 111-117, 1996.
Liu et al., "A general and convenient synthesis of N-aryl piperazines," *Tetrahedrom Letters*, 46: 7921-7922, 2005.
O'Shaughnessy et al, "Synthesis of Pyrrolo- and Pyrido-[1,2-α]benzimidazolequinone Anti-tumor Agents Containing a Fused Cyclopropane Ring," *Synthesis*, 7: 1069-1076, 2005.
Paone et al., "Orally bioavailable imidazoazepanes as calcitonin gene-related peptide (CGRP) receptoragntagonists: Discovery of MK-2918", *Bioorganic and Medicinal Chemistry Letters*, 21:2683-2686, 2011.
Ren et al., "Pharmacophore modeling and virtual screening for the discovery of new transforming growth factor-beta type I receptor (ALK5) inhibitors", *European Journal of Medicinal Chemistry*, 44: 4259-4265, 2009.
Saporita et al, "The Hsp90 Inhibitor, 17-AAG, Prevents the Ligand-Independent Nuclear Localization of Androgen Receptor in Refractory Prostate Cancer Cells," *The Prostate*, 67: 509-520, 2007.
Sasaki et al, "Ring transformation of oxazoles to fused imidazoles. New synthetic route for 6-methyl-2,3-diphenyl-7,8-dihydroimidazo[1,2-b]pyridazine and 5-methyl-2,3-diphenyl-6,7-dihydro-5H-pyrrolo[1,2-a]imidazole, and their perhydrobenzo analogs", *Journal of the Chemical Society, Perkin Transactions 1: Organic and Bio-Organic Chemistry*, 12: 3027-3030, 1983.
Whitlock et al., "Potent and selective $\alpha_{1A}$ adrenoceptor partial agonists—Novel imidazole frameworks," *Bioorganic & Medicinal Chemistry Letters*, 19: 3118-3121, 2009.
CAS RN 1179384-26-9, STN Entry Date: Sep. 2, 2009.
CAS RN 21981-09-3, STN Entry Date: Feb. 19, 2001.
CAS RN 345293-88-1, STN Entry Date: Jul. 11, 2001.
CAS RN 1179381-92-0, STN Entry Date: Sep. 2, 2009.
CAS RN 893704-98-8, STN Entry Date: Jul. 17, 2006.
CAS RN 1179402-21-1, STN Entry Date: Sep. 2, 2009.
CAS RN 312929-26-3, STN Entry Date: Jan. 5, 2001.
CAS RN 326014-86-2, STN Entry Date: Mar. 7, 2001.
CAS RN 344565-06-6, STN Entry Date: Jul. 5, 2001.
CAS RN 790203-53-1, STN Entry Date: Nov. 29, 2004.
CAS RN 475196-08-8, STN Entry Date: Dec. 5, 2002.
CAS RN 1172844-15-3, STN Entry Date: Aug. 5, 2009.
International Search Report and Written Opinion issued for International Application No. PCT/US2012/059558 dated Jan. 18, 2013.
International Search Report and Written Opinion issued for International Application No. PCT/US2014/056369 dated Jan. 14, 2015.
Non-Final Office Action issued for U.S. Appl. No. 15/457,782 dated Oct. 24, 2017.

* cited by examiner

SID 14730725     SID 14742211     SID 3712502

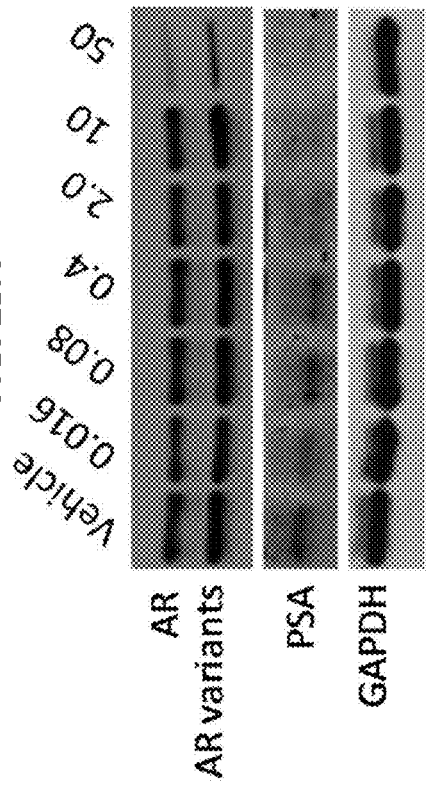
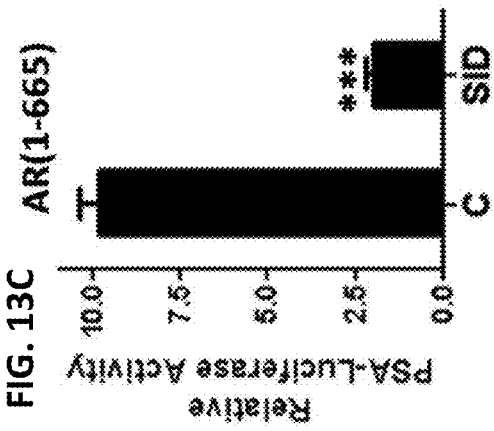
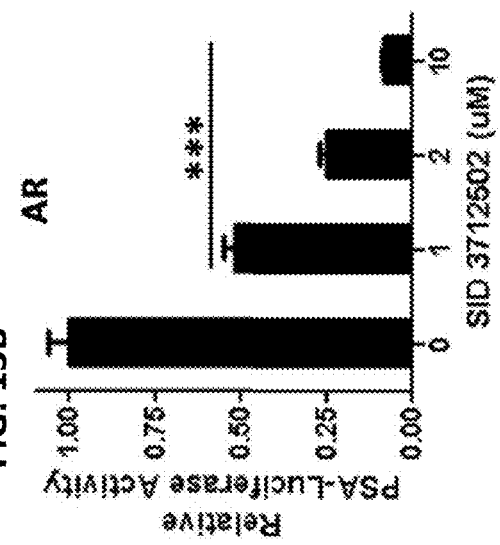

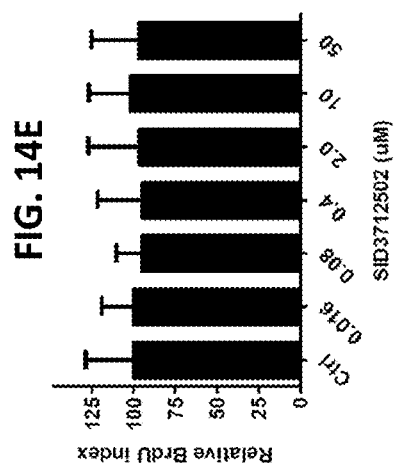
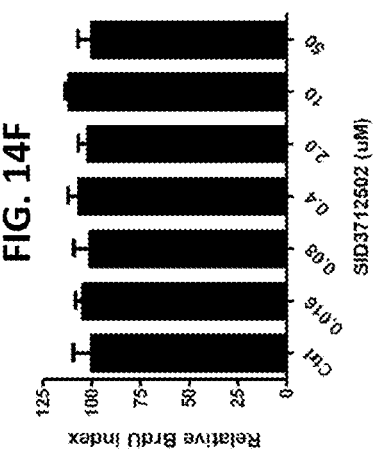
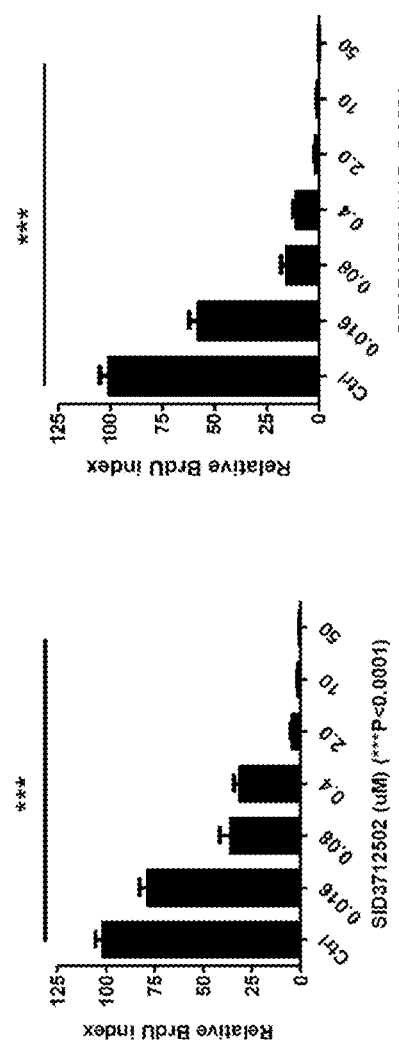
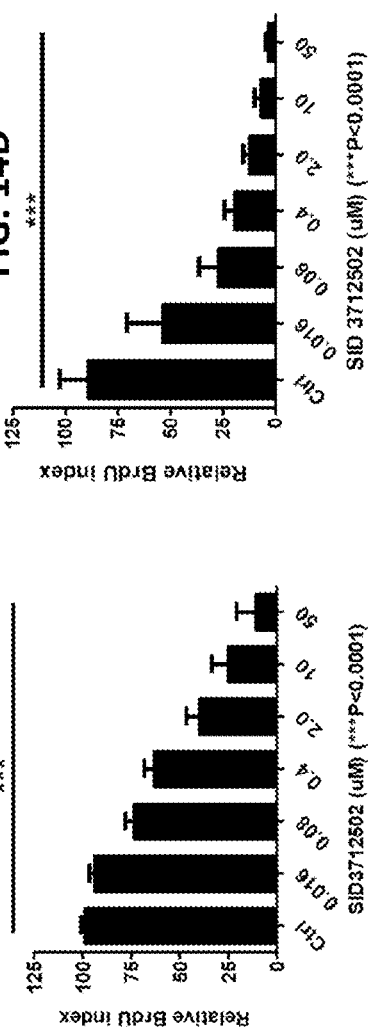

FIG. 16A

Supplemental Table 1

Analogs of Compound #10 - SID 3712502 -

| | Compound Name | Structure | SMILES | MW | Formula | Amount (mg) | Amount (mmol) |
|---|---|---|---|---|---|---|---|
| A | EMS387-023 | 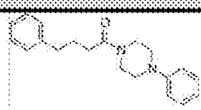 | O=C(CCCC1=CC=CC=C1)N2CCN(C3=CC=CC=C3)CC2 | 308.42 | C20H24N2O | 1.82 | 0.00590 |
| B | EMS387-016 | 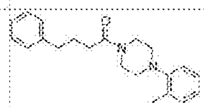 | O=C(CCCC1=CC=CC=C1)N2CCN(C3=CC=CC(C)=CC3)CC2 | 322.44 | C21H26N2O | 3.84 | 0.01191 |
| C | EMS387-020 | 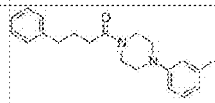 | O=C(CCCC1=CC=CC=C1)N2CCN(C3=CC=CC(C)=C3)CC2 | 322.44 | C21H26N2O | 3.45 | 0.01070 |
| D | EMS387-019 | 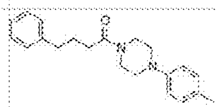 | O=C(CCCC1=CC=CC=C1)N2CCN(C3=CC=C(C)C=C3)CC2 | 322.44 | C21H26N2O | 1.12 | 0.00347 |
| E | EMS387-021 | 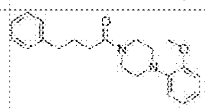 | O=C(CCCC1=CC=CC=C1)N2CCN(C3=CC=CC=C3OC)CC2 | 338.44 | C21H26N2O2 | 5.06 | 0.01495 |
| F | EMS387-024 | 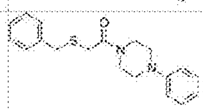 | O=C(CSCC1=CC=CC=C1)N2CCN(C3=CC=CC=C3)CC2 | 326.46 | C19H22N2OS | 2.63 | 0.00806 |
| G | EMS387-025 | 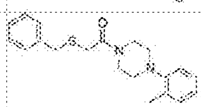 | O=C(CSCC1=CC=CC=C1)N2CCN(C3=CC(C)C=CC=C3)CC2 | 340.48 | C20H24N2OS | 3.63 | 0.01066 |
| H | EMS387-026 | 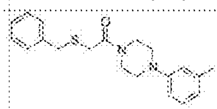 | O=C(CSCC1=CC=CC=C1)N2CCN(C3=CC=CC(C)=C3)CC2 | 340.48 | C20H24N2OS | 3.38 | 0.00993 |
| I | EMS387-027 | 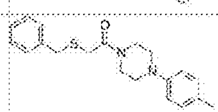 | O=C(CSCC1=CC=CC=C1)N2CCN(C3=CC=C(C)C=C3)CC2 | 340.48 | C20H24N2OS | 1.82 | 0.00535 |
| J | EMS387-028 | 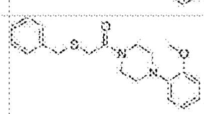 | O=C(CSCC1=CC=CC=C1)N2CCN(C3=CC=CC=C3OC)CC2 | 356.48 | C20H24N2O2S | 6.40 | 0.01795 |
| K | EMS387-030 | 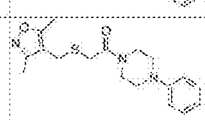 | O=C(CSCC3=C(C)ON=C1C)N2CCN(C3=CC=CC=C3)CC2 | 345.46 | C18H23N3O2S | 2.64 | 0.00764 |

FIG. 16B

| | | | | | | | |
|---|---|---|---|---|---|---|---|
| L | EMS387-031 | | | O=C(CSCC1=C(C)ON=C1C)N2CCN(C3=CC=CC=C3C)CC2 | 359.49 | C19H25N3O2S | 2.74 | 0.00762 |
| M | EMS387-032 | | | O=C(CSCC1=C(C)ON=C1C)N2CCN(C3=CC=CC(C)=C3)CC2 | 359.49 | C19H25N3O2S | 2.28 | 0.00634 |
| N | EMS387-033 | | | O=C(CSCC1=C(C)ON=C1C)N2CCN(C3=CC=C(C)C=C3)CC2 | 359.49 | C19H25N3O2S | 1.85 | 0.00493 |
| O | EMS387-034 | | | O=C(CSCC1=C(C)ON=C1C)N3CCN(C3=CC=CC=C3OC)CC2 | 375.49 | C19H25N3O3S | 2.55 | 0.00679 |
| P | SID 4248943-6 | | | O=C(C1CCN(CC2=C(C)C(C3=CC=C(CC)C=C3)=N3)CC1)N4CCN(C5=CC=CC=C5)CC4 | 472.62 | C29H36N4O2 | 1.56 | 0.00330 |

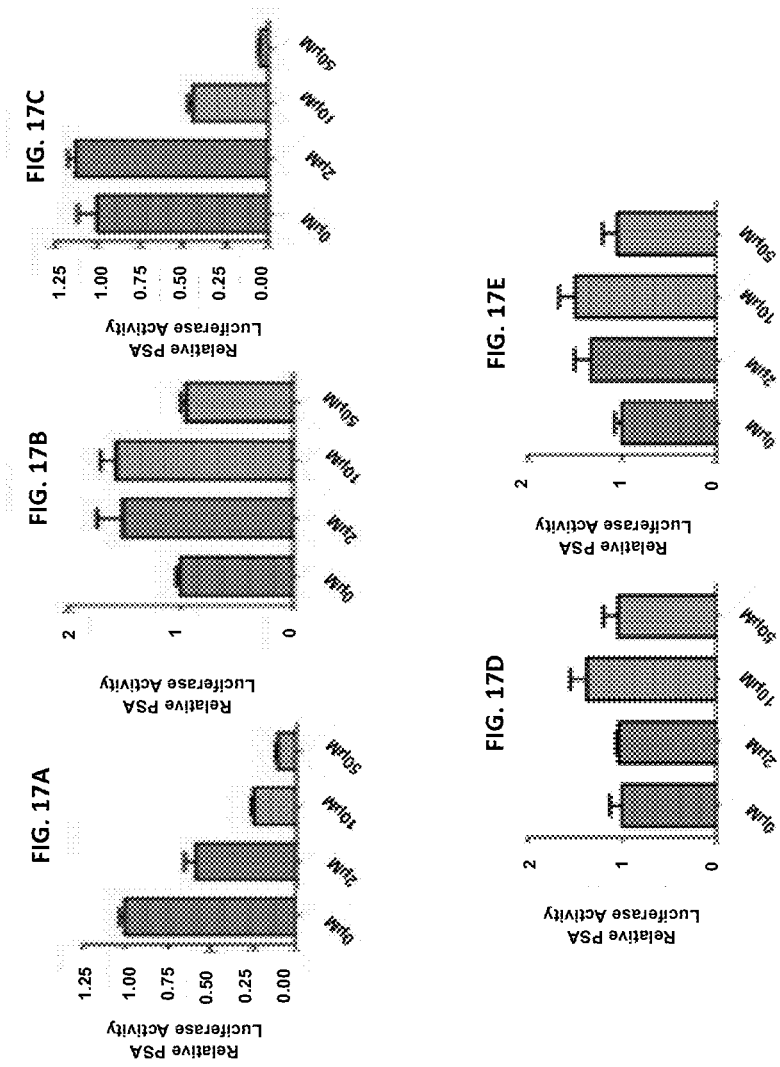

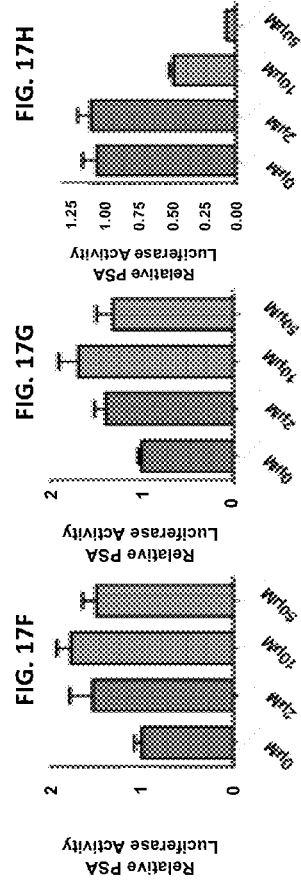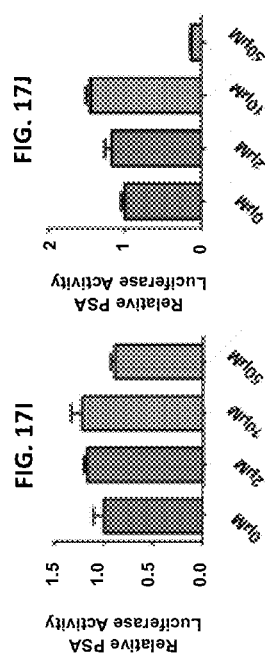

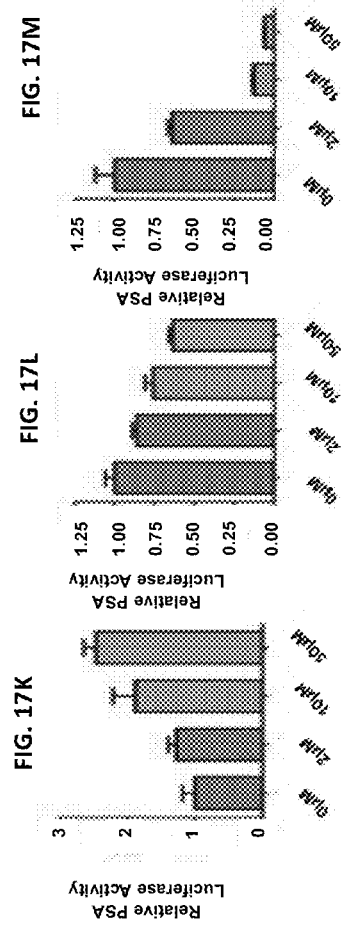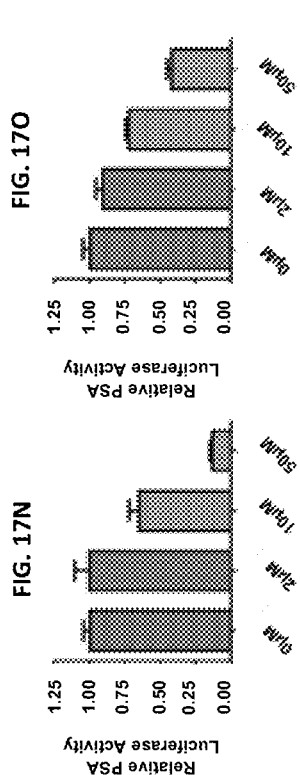

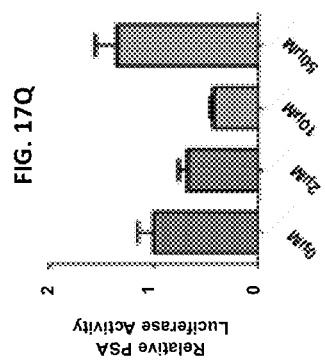
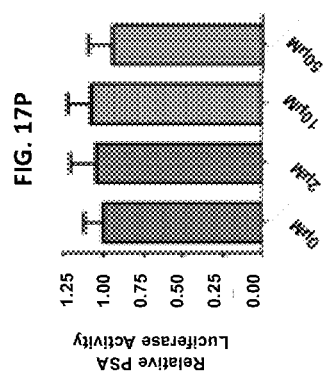

SMALL MOLECULES TARGETING ANDROGEN RECEPTOR NUCLEAR LOCALIZATION AND/OR LEVEL IN PROSTATE CANCER

CROSS REFERENCE TO RELATED APPLICATION

This application is a divisional of U.S. application Ser. No. 14/351,126, filed Apr. 10, 2014, which is the U.S. National Stage of International Application No. PCT/US2012/059558, filed Oct. 10, 2012, which was published in English under PCT Article 21(2), which in turn claims the benefit of U.S. Provisional Application No. 61/546,215, filed Oct. 12, 2011. The prior applications are incorporated herein by reference in their entireties.

BACKGROUND

Castration-resistant prostate cancer (CRPC) is currently incurable and makes prostate cancer the second most common cause of cancer death among men in the United States. Multiple studies have shown that the androgen receptor (AR) is activated via multiple mechanisms including AR overexpression, mutation, hypersensitization, and/or intra-tumoral androgen synthesis in patients relapsed after androgen deprivation therapy (ADT). Overexpression and knockdown studies have demonstrated that AR is a key molecular determinant and an excellent therapeutic target for CRPC. Abiraterone, a potent inhibitor of testosterone synthesis, and MDV3100, a novel AR antagonist, are still effective in the treatment of CRPC, indicating that AR remains a viable target in the majority of CRPC patients.

Androgen receptor (AR), a member of the steroid receptor superfamily, is a ligand-dependent transcription factor that controls the expression of androgen-responsive genes. Intracellular trafficking is an important mechanism in the regulation of many transcription factors, including AR. In order to access its target genes, a transcription factor requires localization to the nucleus. Retention of a transcription factor in the cytoplasm prevents its activity. Thus, a key regulatory step in the action of AR is its nuclear translocation. In androgen-sensitive cells, AR is localized to the cytoplasm in the absence of ligand. Upon addition of androgens, AR translocates to the nucleus and transactivates target genes. However, in CRPC cells, AR remains in the nucleus even in the absence of androgen and transactivates androgen-responsive genes, leading to uncontrolled growth of prostate tumors. Therefore, novel approaches that can block the nuclear localization of AR may provide an effective therapy against CRPC.

SUMMARY

Disclosed herein is a method for treating prostate cancer in a subject, comprising administering a therapeutically effective amount of at least one agent to the subject, wherein the agent is selected from:

(a) a phenyl-substituted imidazole, or a pharmaceutically acceptable salt or ester thereof; or (b) a compound, or a pharmaceutically acceptable salt or ester thereof, having a formula I of:

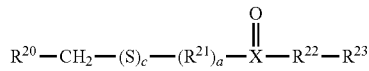

wherein $R^{20}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

$R^{21}$ is an alkanediyl or a substituted alkanediyl;

a is 0 or 1;

c is 0 or 1;

X is C or S;

$R^{22}$ is a moiety that includes at least one divalent amino radical; and $R^{23}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group.

Also disclosed herein is a compound, or a pharmaceutically acceptable salt or ester thereof, having a structure of formula II:

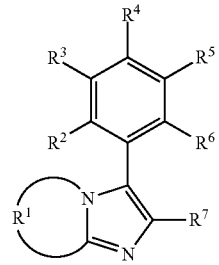

wherein $R^1$ forms a ring structure selected from an optionally substituted single ring that includes four to six C ring atoms, or an optionally substituted polycyclic ring that includes five to ten C ring atoms;

$R^2$ to $R^6$ is each individually H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group; and $R^7$ is H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group, with the proviso that the compound of formula II is not:

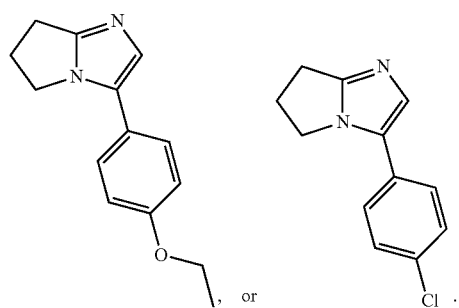 [SMILES: CCOc1ccc(-c2cnc3n2CCC3)cc1 ; Clc1ccc(-c2cnc3n2CCC3)cc1]

Further disclosed herein is a compound, or a pharmaceutically acceptable salt or ester thereof, having a structure of formula I:

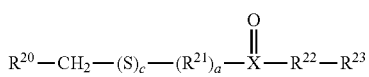

wherein R[20] is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

R[21] is an alkanediyl or a substituted alkanediyl;

a is 0 or 1;

c is 0 or 1;

X is C or S;

R[22] is a moiety that includes at least one divalent amino radical; and

R[23] is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group, with the proviso that the compound of formula I is not:

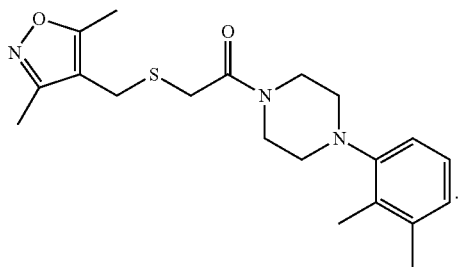

The foregoing will become more apparent from the following detailed description, which proceeds with reference to the accompanying figures.

BRIEF DESCRIPTION OF THE DRAWINGS

FIG. 2A shows representative images of GFP-AR in the indicated cell lines in the absence or presence of 1 nM synthetic androgen mibolerone. PC3, LNCaP, and C4-2 cells were transfected with GFP-AR and localization was assessed in ligand-free conditions or in the presence of mibolerone by fluorescence microscopy within 24 hours of transfection. The results in FIG. 2B are from five transfections for each cell line in the absence of androgen. At least 50 cells were counted after each transfection. Error bars represent±SEM. A P-value<0.05 was generated using an unpaired t-test in GraphPad Prism (GraphPad Software, Inc).

FIG. 3A. C4-2 cells were transfected with GFP-AR and treated with 300 nM 17-AAG, or DMSO in ligand-free conditions. Localization was assessed by fluorescence microscopy 4 hours after treatment. FIG. 3B. Localization of endogenous AR in C4-2 cells treated with 300 nM 17-AAG or DMSO was determined by indirect immunofluorescence.

FIG. 6A. Structures of compounds SID 14730725 (3-(4-Ethoxy-phenyl)-6,7-dihydro-5H-pyrrolo[1,2-a]imidazole), SID 14742211 (3-(4-Chloro-phenyl)-6,7-dihydro-5H-pyrrolo[1,2-a]imidazole) and SID 3712502 (2-[(3,5-dimethyl-1,2-oxazol-4-yl)methylsulfanyl]-1-[4-(2,3-dimethylphenyl)piperazin-1-yl]ethanone). FIG. 6B. Effect of SID 14730725 and SID 3712502 at indicated concentrations (uM) on nuclear localization of AR in castration-resistant C4-2 prostate cancer cells cultured in complete RPMI media with 10% FBS. C4-2 cells were transfected with GFP-AR and subcellular localization of GFP-AR was determined after overnight treatment using fluorescent microscopy. FIG. 6C. Quantitative analysis of results in FIG. 6B. The percent of transfected cells displaying predominant nuclear localization of GFP-AR at in the presence of various concentrations of SID 14730725 and SID 3712502 were determined. FIG. 6D. SID 14730725 inhibited endogenous AR nuclear localization in C4-2 cells. Endogenous AR was detected by immunofluorescent staining using AR antibody N-20 (Santa Cruz Biotechnology). Nuclei were stained with Hoechst.

FIG. 9A. SID 14730725 inhibits the growth of castration resistant C4-2 xenograft tumors. C4-2 tumors were established by sc injection of 1×10[6] cells resuspended in 0.25 ml RPMI complete media mixed with 0.25 ml of Matrigel into young adult male SCID mice. SCID mice were castrated and randomized when C4-2 tumor volume reach ~200 ul. Mice received s.c. delivery of SID 14730725 (50 mg/Kg body weight) or vehicle control (corn oil) every other day for 2 weeks, beginning 4 days after castration. Each group consisted of 7 mice. Tumor volumes were measured using micro-calipers and calculated using the formula (length×width²)/2. FIG. 9B. Body weight of animals was measured every other day. Bars represent the mean±SEM; **p<0.01; Red lines represent data from the animals treated with SID 14730725.

FIGS. 13A-C. Effect of SID 3712502 on the expression of AR and PSA in 22Rv1 (FIG. 13A) cells. Similar results were observed in LNCaP and LAPC4 cell lines (data not shown). The cells in RPMI 1640 complete medium were treated with SID 3712502 or vehicle DMSO at the indicated concentrations (uM) for 48 h. The cells were then harvested in RIPA buffer for Western blot analysis using antibodies for AR, PSA, and GAPDH. GAPDH was included as a loading control. FIG. 13B. SID 3712502 inhibits AR transactivation of PSA-luciferase reporter. C4-2 cells were transfected with PSA6.1-Luc, GFP-AR, and pRL-CMV and then treated with indicated doses of SID 3712502 for 24 hours. FIG. 13C. SID 3712502 inhibits transactivation of PSA-luciferase reporter by AR(1-665), which lacks LBD. PC3 cells were transfected with GFP-NAR and PSA6.1 Luc overnight prior to treatment with 10 µM SID 3712502 (SID) or DMSO (C) for 24 hours. For luciferase assays, cells were lysed with passive lysis buffer (Promega) and both Firefly and *Renilla* luciferase activities were read using a Dual-Luciferase Reporter Assay kit (Promega) on a LmaxII384 luminometer (Molecular Devices). Firefly luciferase values were normalized to *Renilla* (pRL-CMV) or protein of cell lysates. Plotted values represent averaged normalized Firefly luciferase activities, each performed in triplicate, relative to DMSO control. One-way ANOVA was performed with a Bonferroni's Multiple Comparison posttest * p<0.0001 (C). Student's t-test was performed; *p=0.0002 (D).

FIGS. 14A-F. Effect of SID 3712502 at indicated concentrations on BrdU incorporation in cultured AR-positive LNCaP (FIG. 14A), C4-2 (FIG. 14B), 22Rv1 (FIG. 14C), LAPC4 (FIG. 14D) cells, and AR-negative DU145 (FIG. 14E) and PC3 (FIG. 14F) cells. Cells were plated in 12-well plates at 2,500 cell per well in RPMI 1640 complete medium. After 24 hrs, the cells were treated with SID 3712502 at the indicated concentrations for 48 hrs and BrdU incorporation was assayed according to manufacturer's instructions (Invitrogen BrdU staining kit; catalog #: 93-3943). The percentage of BrdU-positive cells was determined and then normalized to generate relative BrdU index. Ctrl=DMSO control.

FIGS. 16A-B is a table showing analogs of SID 3712502.

FIGS. 17A-Q. C4-2 cells were transfected with PSA6.1-Luc, GFP-AR, and pRL-CMV and then treated with indicated doses, 0, 2, 10, or 50 uM of SID 3712502 or its analogs for 24 hours. For luciferase assays, cells were lysed with passive lysis buffer (Promega) and both Firefly and *Renilla* luciferase activities were read using a Dual-Luciferase Reporter Assay kit (Promega) on a LmaxII384 luminometer (Molecular Devices). Firefly luciferase values were normalized to *Renilla* (pRL-CMV) Plotted values represent averaged normalized Firefly luciferase activities, each performed in triplicate, relative to DMSO control.

DETAILED DESCRIPTION

Figure 1:
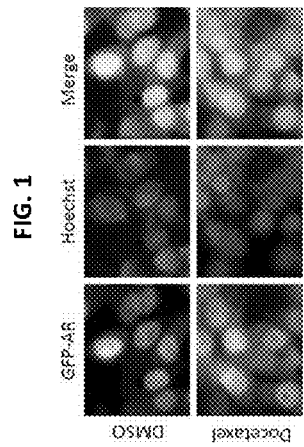
FIG. 1. Docetaxel does not inhibit GFP-AR nuclear localization in C4-2 cells. The images were acquired 24 hours after the treatment of docetaxel at 5 uM or vehicle DMSO. C4-2 cells stably transfected with GFP-AR were changed to phenol red-free RPMI with 10% charcoal-stripped FBS medium before the addition of docetaxel. Nuclei of the cells were stained with Hoechst dye. Images were acquired by fluorescent microscopy.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

"Alkanediyl" or "cycloalkanediyl" refers to a divalent radical of the general formula —$C_nH_{2n}$— derived from aliphatic or cycloaliphatic hydrocarbons.

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)

alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

The term "alkylaryl" refers to a group in which an alkyl group is substituted for a hydrogen atom of an aryl group. An example is —Ar—R, wherein Ar is an arylene group and R is an alkyl group.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "amide" or "amido" is represented by the formula —C(O)NRR', where R and R' independently can be a hydrogen, alkyl, alkenyl, alkynyl, aryl, arylalkyl, cycloalkyl, halogenated alkyl, or heterocycloalkyl group described above. A suitable amido group is acetamido.

The term "amine" or "amino" refers to a group of the formula —NRR', where R and R can be, independently, hydrogen or an alkyl, alkenyl, alkynyl, aryl, arylalkyl, carbonyl (e.g, —C(O)R", where R" can be hydrogen, an alkyl, alkenyl, alkynyl, aryl, or an arylalkyl), cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, arylalkyl, cycloalkyl, cycloalkylalkyl, alkanoyl, alkoxycarbonyl, aralkoxycarbonyl and the like. An aminocarbonyl group may be —C(O)—N(R) (wherein R is a substituted group or H). An "aminocarbonyl" is inclusive of an amido group. A suitable aminocarbonyl group is acetamido.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. Structural analogs are often found using quantitative structure activity relationships (QSAR), with techniques such as those disclosed in Remington (*The Science and Practice of Pharmacology*, 19th Edition (1995), chapter 28). A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aryl" refers to any carbon-based aromatic group including, but not limited to, phenyl, naphthyl, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "arylalkyl" refers to an alkyl group where at least one hydrogen atom is substituted by an aryl group. An example of an arylalkyl group is a benzyl group.

The term "aryl" refers to any carbon-based aromatic group including, but not limited to, benzene, naphthalene, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a group of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COO group. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "co-administration" or "co-administering" refers to administration of an autophagy inducing agent with an autophagy inhibiting agent within the same general time period, and does not require administration at the same exact moment in time (although co-administration is inclusive of administering at the same exact moment in time). Thus, co-administration may be on the same day or on different days, or in the same week or in different weeks. The autophagy inducing agent and the autophagy inhibiting agent may be included in the same composition or they may each individually be included in separate compositions. In certain embodiments, the two agents may be administered during a time frame wherein their respective periods of biological activity overlap. Thus, the term includes sequential as well as coextensive administration of two or more agents.

"Derivative" refers to a compound or portion of a compound that is derived from or is theoretically derivable from a parent compound.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), arylalkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or arylalkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

Some of the compounds described herein may also exist in their tautomeric form.

The term "subject" includes both human and veterinary subjects.

A "therapeutically effective amount" or "diagnostically effective amount" refers to a quantity of a specified agent sufficient to achieve a desired effect in a subject being treated with that agent. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In some embodiments, a substituted group is not substituted with another substituted group (e.g. substituted alkyl is substituted with unsubstituted aryl).

Overview

There is no therapy specifically designed for and capable of effectively blocking AR nuclear localization in CRPC cells. Abiratrone, a newly FDA-approved drug for castration resistant prostate cancer, inhibits testosterone synthesis rather than directly targeting AR. MDV3100, a novel AR antagonist, was reported to impair AR nuclear translocation in prostate cancer cells. However, the nuclear AR signal appeared to be still higher than cytoplasmic AR signal in prostate cancer cells in the presence of MDV3100. A recent study showed that tubulin-targeting therapeutic agents such as docetaxel can inhibit androgen-dependent AR nuclear translocation by targeting AR association with tubulin. However, our preliminary studies showed that docetaxel had no significant effect on AR nuclear localization in castration-resistant C4-2 cells (FIG. 1).

Figure 2A:
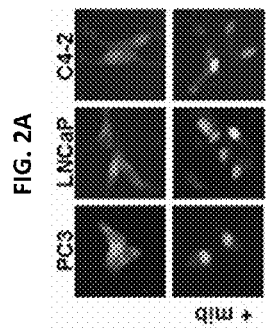
FIGS. 2A and 2B. Localization of GFP-AR in AR-negative PC3, androgen-sensitive LNCaP, and CRPC C4-2 cells.
Figure 2B:
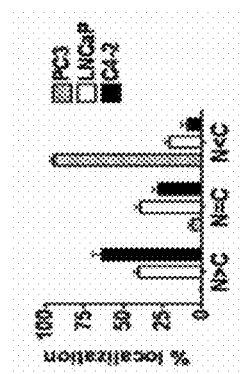

Unliganded androgen receptor (AR) is localized to the nucleus in CRPC cells. A prerequisite for AR transcriptional activity is its nuclear localization. To determine whether the subcellular localization of AR was altered during the progression to castration-resistance, AR-negative PC3 prostate cancer cells, androgen-sensitive LNCaP cells and castration-resistant C4-2 cells were transfected with AR tagged to green fluorescent protein (GFP) and localization was assessed by fluorescence microscopy in hormone-free conditions. Notably, GFP-AR exhibits similar androgen-binding affinity as does untagged AR, and androgen can induce GFP-AR transactivation. As previously described, the localization of GFP-AR in PC3 cells is regulated by androgens. In the absence of ligand, GFP-AR was predominantly cytoplasmic in nearly all PC3 cells, with no observed cells exhibiting predominantly nuclear localization (FIG. 2). Less than half (40%) of transfected LNCaP cells displayed predominant nuclear localization of GFP-AR. In CRPC C4-2 cells, however, GFP-AR exhibited predominant nuclear localization in 64% of transfected cells, a significant increase (P<0.05) compared to LNCaP cells (FIG. 2). This is consistent with a previous report in which increased nuclear localization of endogenous AR in C4-2 cells compared to the parental LNCaP cell line was observed by immunocytochemistry. Treatment with 1 nM mibolerone, a synthetic androgen, induced complete nuclear localization of GFP-AR in PC3, LNCaP, and C4-2 cells (FIG. 2A). No differences were observed between the cell lines when transfected with GFP alone, which was highly expressed in both the nucleus and cytoplasm (data not shown), suggesting that the differences in GFP-AR localization were due to the presence of AR rather than altered localization of GFP.

Figure 3A:
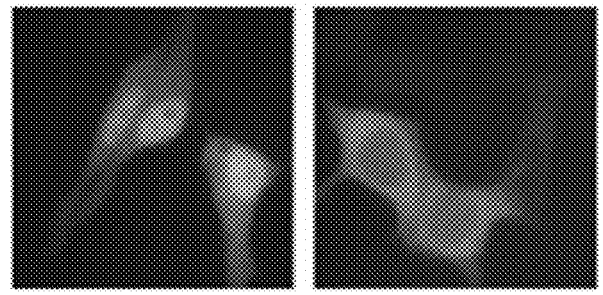
FIGS. 3A and 3B. Effect of the hsp90 inhibitor 17-AAG on AR localization and activity in C4-2 CRPC cells.
Figure 3B:
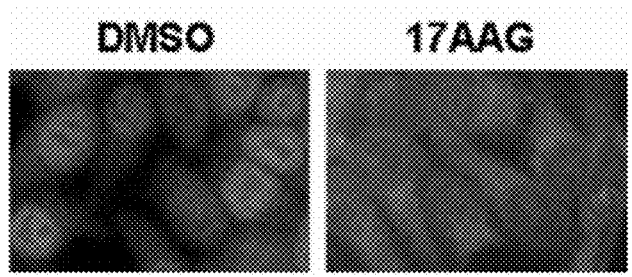

Hsp90 plays an important role in ligand-induced AR nuclear translocation. To determine whether hsp90 also regulates the ligand-independent nuclear localization of AR, castration-resistant C4-2 cells were transfected with GFP-AR and treated with the hsp90 inhibitor, 17-AAG. After four hours in the presence of 300 nM 17-AAG, the localization of GFP-AR had shifted from predominantly nuclear to cytoplasmic (FIG. 3A). The nuclear localization of GFP-AR in C4-2 cells was also prevented by two other hsp90 inhibitors, geldanamycin and radicicol (data not shown). To determine if the effect of hsp90 inhibition on endogenous AR in C4-2 cells was similar to its effect on transfected GFP-AR, immunofluorescence experiments were performed. Under hormone-free conditions, endogenous AR is present in the nucleus of C4-2 cells; however, after 17-AAG treatment, a decrease in nuclear AR expression was observed (FIG. 3B). Thus, the ligand-independent nuclear localization of both endogenous AR and transfected GFP-AR in castration-resistant C4-2 cells can be prevented when hsp90 is inhibited.

Figure 4:
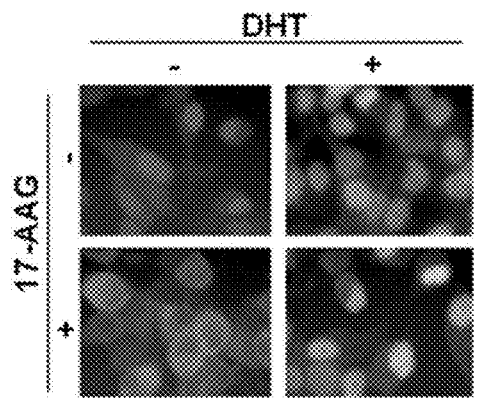
FIG. 4. Responsiveness of GFP-AR in a representative C4-2 subline to DHT and 17-AAG. C4-2 cells were transfected with ApaL1 linearized pEGFP-C1-AR plasmid and stable single clones were picked up after G418 selection. The C4-2 cells were cultured in ligand-free media and treated with DMSO vehicle, 1 nM DHT and/or 100 nM 17-AAG. Localization of GFP-AR signal was assessed by fluorescence microscopy overnight after treatment.

C4-2 cells were transfected with GFP-tagged AR and G418-based selection was used to establish several sublines (C4-2-GFP-AR) that stably express GFP-AR. As expected, GFP-AR in representative stably transfected C4-2 cells behaves the same as the transiently transfected GFP-AR in C4-2 cells (FIG. 4). GFP-AR was predominantly localized to the nucleus in ligand-free media in the stably transfected C4-2 cells. Addition of DHT caused more intense nuclear localization of GFP-AR, indicating its responsiveness to androgens. Also, low-dose 17-AAG (100 nM) caused cytoplasmic localization of GFP-AR under androgen-depleted conditions but not in the presence of 1 nM DHT. These C4-2 sublines were further characterized for optimization of the high throughput screening assay development.

Thus, it was determined that GFP-AR is localized in the nucleus of castration-resistant C4-2 prostate cancer cell lines, and 17-AAG inhibits the ligand-independent nuclear localization of AR in C4-2 cells. Based on these findings, several C4-2 sublines were established that stably express GFP-AR for developing a high throughput screening assay, which is described below in detail in the Examples section. Using the high throughput assay, the University of Pittsburgh Drug Discovery Institute (UPDDI) library was screened resulting in the discovery of several agents that inhibit AR nuclear localization and/or reduce AR levels in castration-resistant prostate cancer as described below in more detail.

Agents

Disclosed herein are agents that can be used for treating prostate cancer, particularly castration-resistant prostate cancer.

One embodiment of the agents are compounds, or a pharmaceutically acceptable salts or esters thereof, having a formula I of:

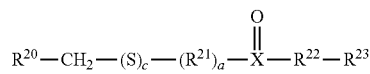

wherein $R^{20}$ is an aryl, substituted aryl, heteroaryl, substituted heteroaryl, heterocycloalkyl, substituted heterocycloalkyl, cycloalkyl, substituted cycloalkyl, alkoxy, aryloxy, a silyl-containing group, a boryl-containing group, a phosphine-containing group, amino, a thio-containing group, a seleno-containing group, halide, or a nitro-containing group;

$R^{21}$ is an alkanediyl or a substituted alkanediyl;

a is 0 or 1;

c is 0 or 1;

X is C or S;

$R^{22}$ is a moiety that includes at least one divalent amino radical; and $R^{23}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group.

In certain embodiments, $R^{20}$ is selected from isoxazolyl, substituted isoxazolyl (e.g, dialkyl-substituted such as dimethyl, hydroxy-substituted, hydroxyalkyl-substituted, or a combination thereof), oxazolyl, substituted oxazolyl (e.g, dialkyl-substituted such as dimethyl, hydroxy-substituted, hydroxyalkyl-substituted, or a combination thereof) cyclohexyl, substituted cyclohexyl (e.g., hydroxy-substituted cyclohexyl), piperidinyl, substituted piperidinyl (e.g., hydroxy-substituted piperidinyl), oxacyclopentyl, substituted oxacyclopentyl (e.g., hydroxyalkyl-substituted), oxacyclohexanyl, substituted oxacyclopentyl (e.g., hydroxyalkyl-substituted), thiophenyl, substituted thiophenyl (e.g., hydroxyalkyl-substituted), phenyl, substituted phenyl (e.g., hydroxyalkyl-substituted), pyridinyl, substituted pyridinyl (e.g., hydroxyalkyl-substituted), indolyl, substituted indolyl (e.g., hydroxyalkyl-substituted), furanyl, substituted furanyl (e.g., hydroxyalkyl-substituted), imidazolyl, substituted imidazolyl (e.g., hydroxyalkyl-substituted); $R^{21}$ is selected from $C_1$-$C_3$ alkanediyl or substituted $C_1$-$C_3$ alkanediyl (e.g., alkyl-substituted such as methyl or dimethyl); a is 1; X is C; $R^{22}$ is selected from:

$R^{23}$ is selected from phenyl, substituted phenyl (e.g., alkyl-substituted phenyl such as dimethyl-substituted, or amino-substituted, or aminoalkyl-substituted), piperidinyl, substituted piperidinyl (e.g., amino-substituted), furanyl, substituted furanyl (e.g., aminoalkyl-substituted or amino-substituted), pyridinyl, substituted pyridinyl (e.g., aminoalkyl-substituted or amino-substituted), pyrimidinyl, substituted pyrimidinyl (e.g., aminoalkyl-substituted or amino-substituted), naphthenyl, substituted naphthenyl, (e.g., aminoalkyl-substituted or amino-substituted), thiazole, substituted thiazole (e.g., aminoalkyl-substituted or amino-substituted); isoindazolyl, substituted isoindazolyl (e.g., amino-alkyl-substituted or amino-substituted); triazolyl, or substituted triazolyl (e.g., aminoalkyl-substituted or amino-substituted).

In preferred embodiments, $R^{20}$ is substituted isoxazolyl, c is 1; a is 1; $R^{21}$ is —$CH_2$—, X is C, $R^{22}$ is:

and $R^{23}$ is substituted phenyl.

In other preferred embodiments, X is C; $R^{22}$ is:

and $R^{23}$ is substituted phenyl.

In certain embodiments, $R^{20}$ is phenyl.

In certain embodiments, $R^{22}$ is:

In certain embodiments, $R^{20}$ is an aryl or substituted aryl; c is 1; a is 1; $R^{21}$ is —$CH_2$—, X is C, $R^{22}$ is:

and $R^{23}$ is substituted phenyl.

In certain embodiments, $R^{20}$ is an aryl or substituted aryl; c is 0; a is 1; $R^{21}$ is —$CH_2CH_2$—, X is C, $R^{22}$ is:

and $R^{23}$ is Substituted Phenyl.

Illustrative compounds of formula I, including SID3712502, are shown in FIG. 16. Particularly preferred compounds include SID3712502,

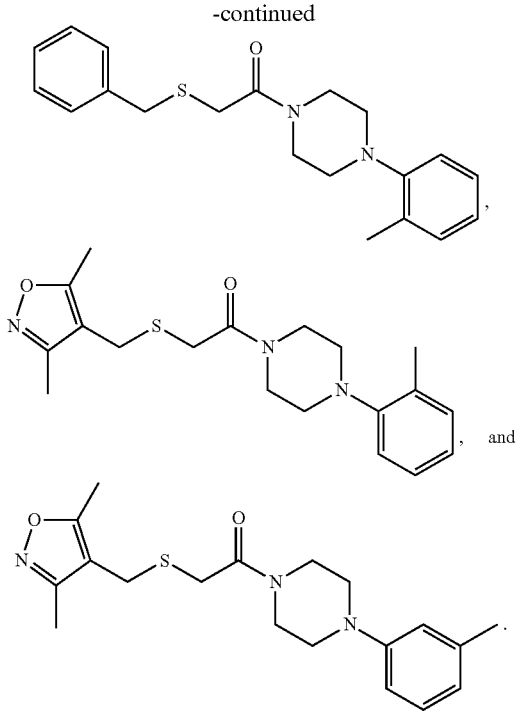

Figure 11:
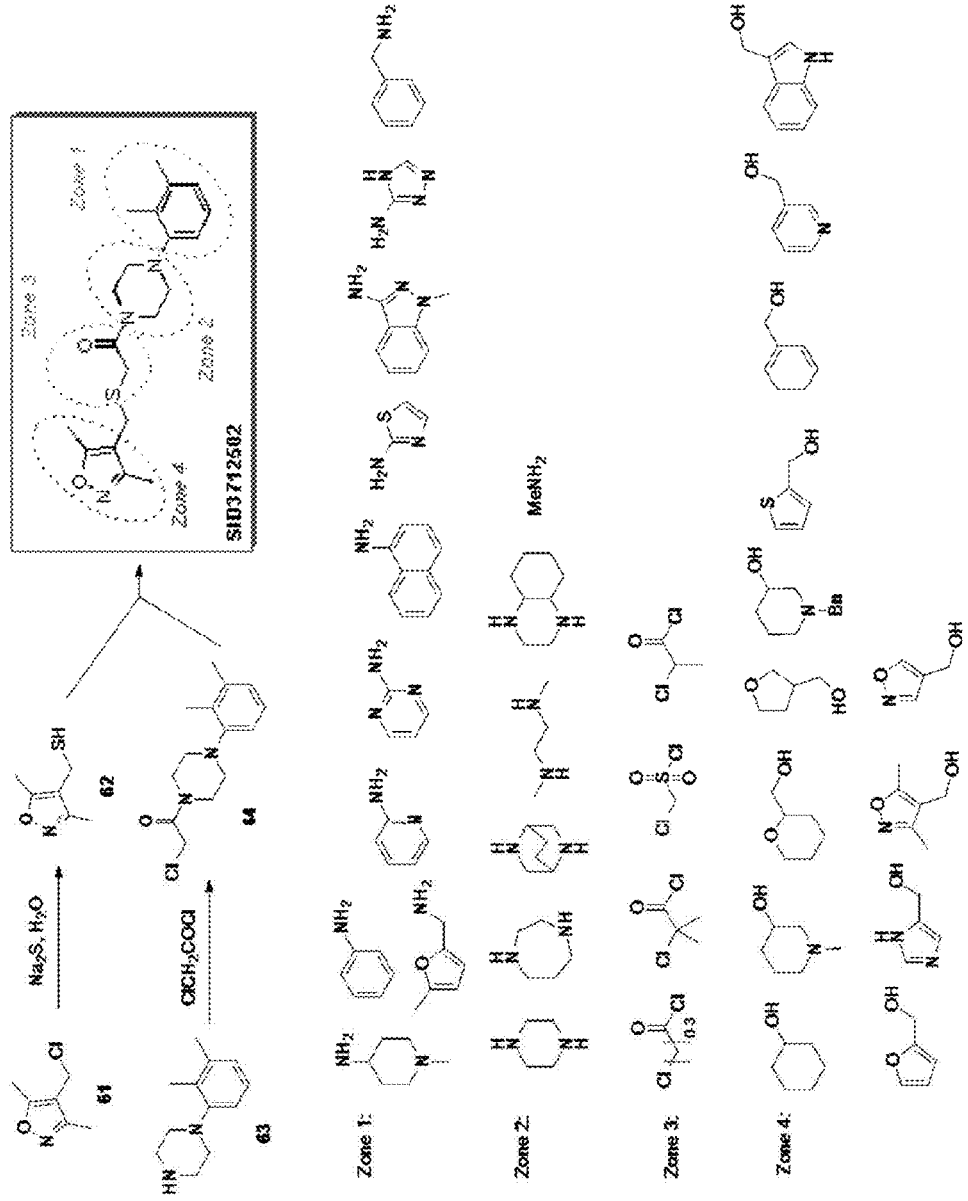
FIGS. 11 and 12 are synthetic schemes for making agents as disclosed herein.

An illustrative scheme 1 for making the compounds of formula I is shown in FIG. 11. Scheme 1 shows a synthesis of the parent structure that is amenable to the modifications lined out in a zone model. Isoxazole 61 can be obtained from the chloromethylation of 3,5-dimethylisoxazole, or via the corresponding alcohol, and will be converted to thiol 62. In situ alkylation of 62 with chloride 64 under the basic conditions of thiol formation leads to the parent hit, SID3712502. There are many methods known for pyridazine synthesis, and the preparation of 63 will follow one of these methods, most likely starting with the aniline Acylation of 63 with chloroacetyl chloride provides 64. The building blocs shown in Scheme 1 for zones 1 and 4 have been selected to cover a large range of chemical diversity; in addition, they are commercially available and are therefore readily funneled into the segment-based synthesis plan. Zone 2 contains a few diamines that preserve the distance between zone 1 and zone 3, i.e. where the nitrogens are appropriately spaced, but this zone will also be contracted to a simple nitrogen linker in order to probe the need to maintain the overall distance and orientation between zone 1 and zone 4. Zone 3 contains another spacer functionality, but the amide carbonyl group might also be involved in specific interactions with the binding site on the protein. Therefore, the distance between the carboxyl function and the halide electrophile will be varied, and the carbonyl group will also be replaced by a sulfonyl function. Finally, not shown in Scheme 1 are planned analogs where the thioether atom is replaced by an ether and N-methyl function.

Also disclosed herein is a further group of compounds, or pharmaceutically acceptable salts or esters thereof, that can be used for treating prostate cancer, particularly castration-resistant prostate cancer. This group of compounds includes a phenyl-substituted imidazole scaffold moiety. More particularly, the phenyl-substituted imidazole may be a phenyl-substituted pyrroloimidazole. For example, the phenyl-substituted pyrroloimidazole may include a 6,7-dihydro-5H-pyrrolo[1,2-a]imidazole moiety. The 6,7-dihydro-5H-pyrrolo[1,2-a]imidazole moiety may be substituted at the 3 position with a phenyl or substituted phenyl group. In certain embodiments, the phenyl substituent is located at the para position relative to the position of the phenyl-pyrroloimidazole bond. Examples of phenyl substituents include halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group.

Illustrative phenyl-substituted imidazole compounds have a formula II of:

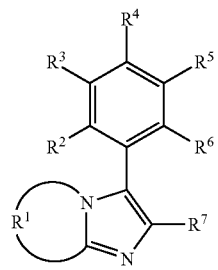

wherein $R^1$ forms a ring structure selected from an optionally substituted single ring that includes four to six C ring atoms (inclusive of the single C ring atom that is also part of the imidazole moiety), or an optionally substituted polycyclic ring that includes five to ten C ring atoms (inclusive of the single C ring atom that is also part of the imidazole moiety);

$R^2$ to $R^6$ is each individually H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group; and $R^7$ is H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group.

In certain embodiments, the compound of formula II may be:

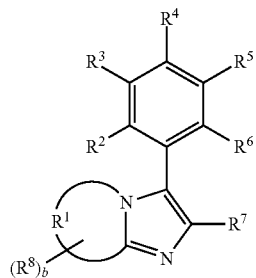

wherein $R^1$-$R^7$ are the same as in formula II; $R^8$ is alkyl, hydroxy, alkoxy, hydroxyalkyl, or alkoxyalkyl; and b is 0 or 1.

In certain embodiments of formula II, the compound has a structure of:

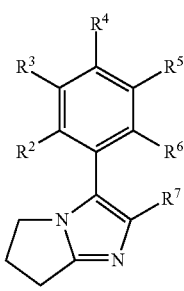

wherein $R^2$, $R^3$, $R^5$ and $R^6$ are each individually H; $R^4$ is halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group (preferably halogen or lower alkoxy); and $R^7$ is H. In this embodiment, R' forms a ring structure that includes four C ring atoms.

$R^4$ is preferably halogen or lower alkoxy.

$R^2$, $R^3$, $R^5$ and $R^6$ are preferably each individually H.

$R^7$ preferably is H.

Figure 12:
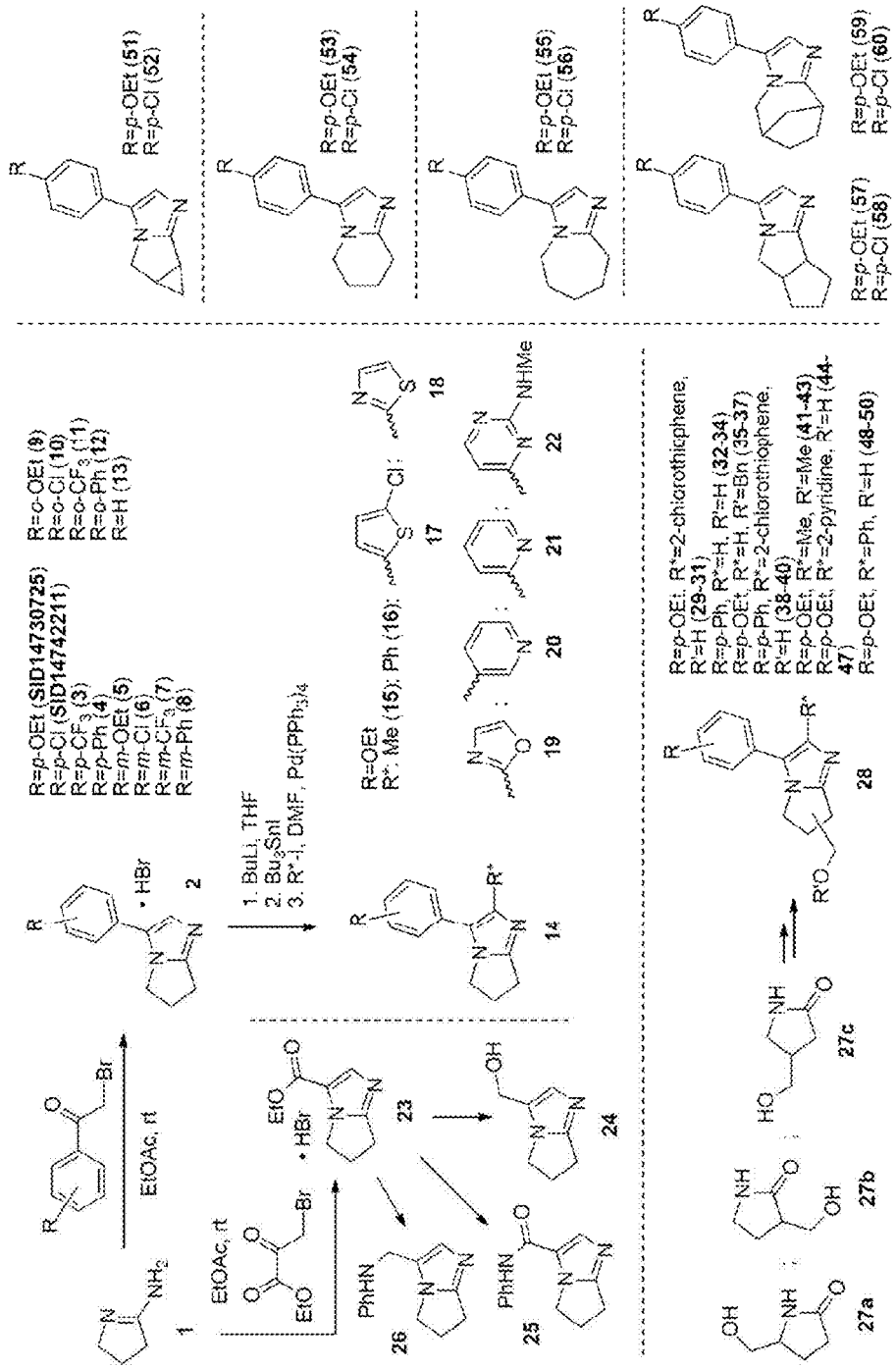

An illustrative synthetic scheme 2 for making the compounds of formula II is shown in FIG. 12. The commercially available amidine 1 may be used to generate the parent structures as well as 11 analogs 3-13 in concise cyclocondensations with bromomethyl ketones. This first series of analogs explores the size and electronics of the arene substituent of hits SID14730725 and SID14742211. In order to introduce a second, vicinal substituent, SID14730725 will be deprotonated at the imidazole ring with BuLi and subjected to a Stille coupling, mainly with heterocyclic building blocks, to access the analog series 15-22. Treatment of 1 with α-bromoethylpyruvate provides access to ester 23, which can be readily converted to alcohol 24, amide 25, and amine 26. In an analogous fashion to the preparation of 2, hydroxymethylene amides 27a-c will be converted to the corresponding amidines and then to pyrroloimidazoles 29-50, which explore the influence of the mainly more polar chains on the pyrrolidine ring. While specific substituents are shown for this series, their chemical structures will depend on the actual activity profile obtained for 2 and 14, i.e. the most active core substitutions will be selected for these $2^{nd}$ generation SAR studies. Finally, we will also explore ring fusions and larger ring replacements of the pyrrolidine subunit as shown for targets 51-60.

In certain embodiments, the agents disclosed herein may have one or more of the following properties:
- AR-GFP $EC_{50}$ (primary assay): ≤10 uM; concentration-dependent, appropriate curve.
- Selective vs. other translocation targets; $EC_{50}$≥5 fold.
- Chemical purity/integrity: >90% pure by LCMS/UV/ELS detection, structure consistent with other analytical data (NMR).
- Mechanism of action: Mechanism is consistent with potency and characterization in cell based assays and does not involve kinase inhibition, DNA binding or unspecific/unknown cytotoxicity.
- Cell Proliferation Assays in AR-positive cells: ≤5 uM; in AR-negative cells: >10 uM.
- ADMET Predictions: Acceptable within Lipinski/Veber Rules, adequate solubility, permeability, low CYP and hERG channel inhibition, etc.
- Half-life in the order of 4-6 h.
- Limited metabolism (i.e. renal elimination).
- Bioavailability greater than 30%.
- Tumor penetration with concentrations maintained in the tumor at or above the $EC_{50}$'s obtained from cell culture.

Pharmaceutical Compositions and Method of Use

The agents disclosed herein may be administered to a subject for treating prostate cancer, particularly castration-resistant prostate cancer. In certain embodiments a subject is identified as having castration-resistant prostate cancer that may be responsive to the agents disclosed herein. For example, patients that are offered any form of androgen deprivation therapy or anti-androgen therapy, including treatment with abiraterone or MDV3100, for the management of prostate cancer would be candidates for treatment with the agents disclosed herein.

Administration of the agent may reduce the nuclear level of androgen receptor in castration-resistant prostate cancer (CRPC) cells relative to the untreated control CRPC cells. Reducing nuclear androgen receptor levels is expected to inhibit its activation. Reduction of androgen receptor activation can be determined via measuring androgen-responsive genes, such as prostate-specific antigen (PSA).

In certain embodiments, the agent may be co-administered with another therapeutic agent such as, for example, an immunostimulant, an anti-cancer agent, an antibiotic, or a combination thereof. In particular, the agents targeting AR nuclear localization could be used in combination with standard androgen deprivation therapy (ADT) or with abiratrone in the treatment of CRPC. For example, SID 14730725 is more effective in blocking AR nuclear localization in the absence or in the presence of very low levels of androgens as described below in detail, which can be achieved by ADT or abiratrone administration.

The agents disclosed herein can be included in a pharmaceutical composition for administration to a subject. The pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The agents disclosed herein can be administered to subjects by a variety of mucosal administration modes, including by oral, rectal, intranasal, intrapulmonary, or transdermal delivery, or by topical delivery to other surfaces. Optionally, the agents can be administered by non-mucosal routes, including by intramuscular, subcutaneous, intravenous, intra-arterial, intra-articular, intraperitoneal, intrathecal, intracerebroventricular, or parenteral routes. In other alternative embodiments, the agents can be administered ex vivo by direct exposure to cells, tissues or organs originating from a subject.

To formulate the pharmaceutical compositions, the agents can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, IN) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The agents can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The agents can be combined with the base or vehicle according to a variety of methods, and release of the agents can be by diffusion, disintegration of the vehicle, or associated formation of water channels. In some circumstances, the agent is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the agents can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the agent can be delivered to a subject in a manner consistent with conventional methodologies associated with management of the disorder for which treatment or prevention is sought. In accordance with the disclosure herein, a prophylactically or therapeutically effective amount of the agent is administered to a subject in need of such treatment for a time and under conditions sufficient to prevent, inhibit, and/or ameliorate a selected disease or condition or one or more symptom(s) thereof.

The administration of the agent can be for either prophylactic or therapeutic purpose. When provided prophylactically, the agent is provided in advance of any symptom. The prophylactic administration of the agents serves to prevent or ameliorate any subsequent disease process. When provided therapeutically, the compound is provided at (or shortly after) the onset of a symptom of disease or infection.

For prophylactic and therapeutic purposes, the agent can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the agent can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosage of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the agent is outweighed in clinical terms by therapeutically beneficial effects. A non-limiting range for a therapeutically effective amount of an agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight. Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

EXAMPLES

High Throughput Screen Assay

Figure 5:
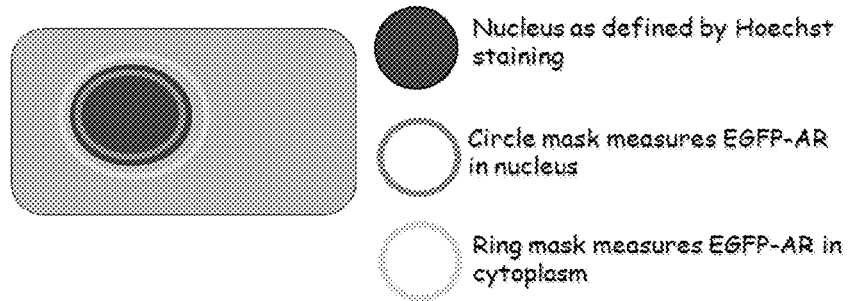
FIG. 5. Molecular translocation algorithm. EGFP translocation=mean [average nuclear EGFP-AR–average cytoplasmic EGFP-AR].
Figure 6A:
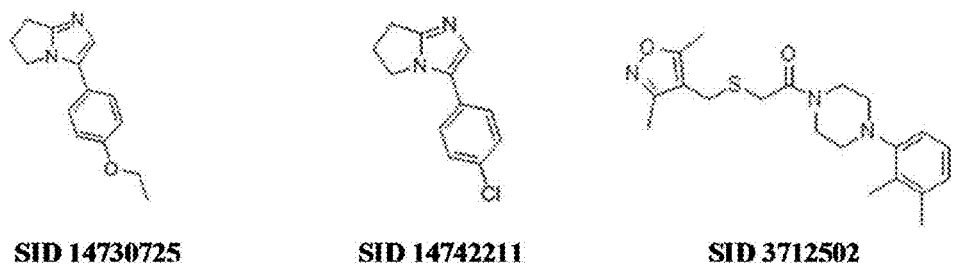
FIGS. 6A, 6B, 6C and 6D.
Figure 6B:
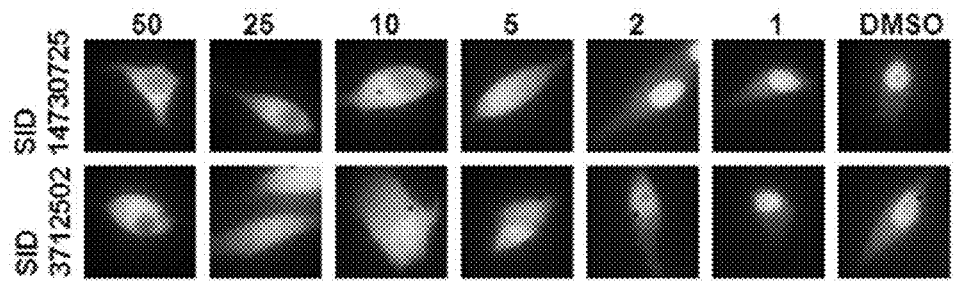
Figure 6C:
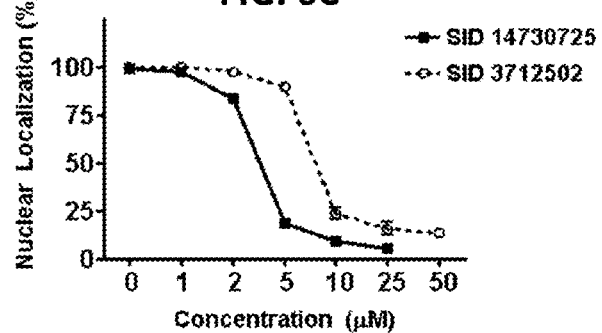
Figure 6D:
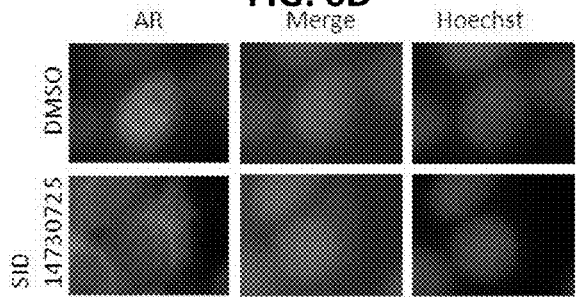

The C4-2-GFP-AR subclone was cultured in 384-well plates in complete RPMI media. We used regular complete media in high throughput assay because it contains castration levels of androgens. Two days after being plated, cells were treated overnight with 17-AAG at 300 nM along with vehicle controls. The treated cells were then briefly fixed and stained with the nucleic acid dye Hoechst 33342 for the nuclei. Hoechst nuclear staining was co-localized with GFP signal in C4-2 cells treated with vehicle only. In contrast, GFP signal in cells treated with 17-AAG was localized to the cytoplasm, and not the nuclear Hoechst stain. Images of GFP signals and Hoechst signals were acquired into separate channels on a Cellomics ArrayScan® V$^{TT}$ system. Both nuclear and cytoplasmic GFP signals were quantified with the ArrayScan V$^{TT}$, which uses an image-based auto-focus system, and has the capability of imaging up to six excitation and emission channels. Channel selection was accomplished using a fast excitation filter wheel combined with a multi-band emission filter. The Cellomics compartmental analysis algorithm was used to quantify the relative distribution of the GFP-AR between nuclear and cytoplasmic cellular compartments. Hoechst was used to stain and identify the nucleus; this fluorescent signal focuses the instrument and defines a nuclear mask. The mask was eroded to reduce cytoplasmic contamination within the nuclear area, and the reduced mask was used to quantify the amount of target channel GFP fluorescence within the nucleus. The nuclear mask was then dilated to cover as much of the cytoplasmic region as possible without going outside the cell boundary. Removal of the original nuclear region from this dilated mask created a ring mask that covers the cytoplasmic region outside the nuclear envelope. The image analysis algorithm provided an output of quantitative data such as the total or average fluorescent intensities of the GFP signal in the nucleus (Circ) or cytoplasm (Ring) on a per cell basis (FIG. 5), that may also be reported as an overall well average value in the presence or absence of 17-AAG. All irregularly shaped nuclei, as well as aggregate cells, were excluded from the analysis. The major criteria for cell subline selection are intensity of the signal, relative nuclear to cytoplasmic distribution, optimal signal:background and Z'-factor, stability of the GFP signal and freeze-thaw endurance of the cells.

Discovery of Agents

Using the automated high throughput and high content screening assay described above, the entire UPDDI compound library (~260,000 small molecules) was initially screened at one concentration (10 uM) to identify potential hits. Each hit compound was then tested at 10 specified concentrations between 1 nM and 50 uM. Again, the hsp90 inhibitor 17-AAG and DMSO vehicle were used as positive and negative controls, respectively, in the high throughput screening.

The screen identified ~30 candidate small molecules that can disrupt GFP-AR nuclear localization in the C4-2 stably-transfected cell line. They were tested further to verify they can indeed disrupt AR nuclear localization in C4-2 cells and to determine whether the inhibition of nuclear localization of GFP-AR is mediated through a general inhibition of nuclear import machinery. Only small molecules that can specifically inhibit GFP-AR nuclear localization and not that of GFP-GR and GFP-ERα were characterized further. Also, the candidate small molecules were tested for their cytotoxicity using a panel of cultured cell lines.

Figure 8A:
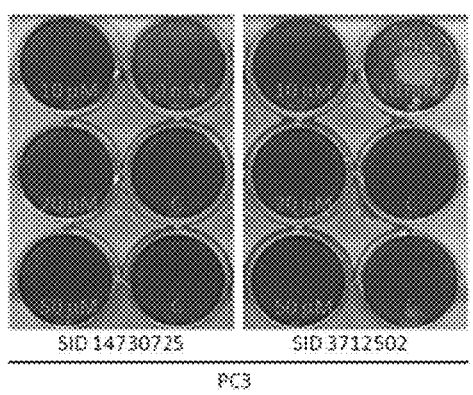
FIGS. 8A and 8B. Effect of SID 14730725 and SID 3712502 on survival of PC3 (FIG. 8A) and C4-2 cells (FIG. 8B). PC3 or C4-2 cells were plated in 12-well plates at 2,500 cell per well in RPMI 1640 complete medium. After 24 hrs, the cells were treated with SID 14730725 or SID 3712502 at the indicated concentrations for 48 hrs. The wells were washed with PBS thrice and fixed in 0.5% crystal Violet in methanol. C=control; treated with vehicle DMSO.
Figure 8B:
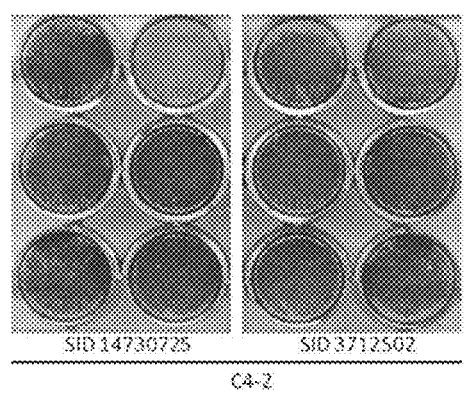

Once the candidate small molecules were identified, they were tested if they indeed can inhibit androgen-independent nuclear localization of GFP-AR and endogenous AR in the C4-2 cells. Also, these agents were tested to see if they are cytotoxic in several different cell lines, including the AR-positive prostate cancer cell lines C4-2, LNCaP, LAPC-4 and AR-negative cell lines PC3 and COS-1 (FIG. 8). These assays led to the identification of 3 agents that specifically target androgen-independent AR nuclear localization in prostate cancer cells and have minimal cytotoxicity on other types of cells.

Figure 7:
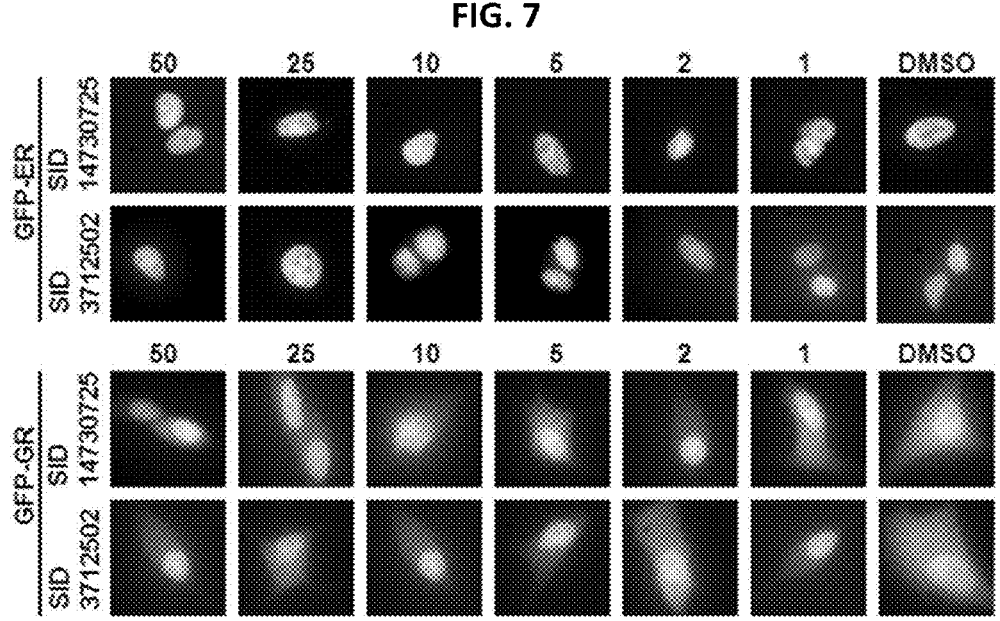
FIG. 7. The effect of SID 14730725 and SID 3712502 on nuclear localization of GFP-ER (Top panel) and GFP-GR (Bottom panel) in C4-2 cells. C4-2 cells were transfected with GFP-ER or GFP-GR overnight. The following day the cells were treated with different concentrations (uM) of the small molecules. The cells transfected with GFP-GR were co-treated with 0.5 μM Dexamethasone. Cells were imaged 24 hours after the treatment with the small molecules.

The agents are specific in inhibiting AR nuclear localization. FIG. 6 shows that treatment with SID 14730725 or SID 3712502 effectively inhibited GFP-AR nuclear localization in transfected C4-2 cells but had no effect on the localization of GFP-GR or GFP-ER (FIG. 7), suggesting the inhibition of nuclear localization of AR in CRPC cells by SID 14730725 or SID 3712502 is specific. The inhibition of SID 14730725 on endogenous AR nuclear localization in the C4-2 cell line was also demonstrated (FIG. 6D; the effect of SID 3712502 on endogenous AR nuclear localization has not been tested yet.). Unlike GFP-AR, which is wild-type, the endogenous AR in C4-2 cells contains a point mutation in its ligand-binding domain. This observation suggests that SID 14730725 can block nuclear localization of both wild-type and mutant AR in CRPC cells.

The agents had little or no cytotoxicity. One important consideration for selecting small molecular agents is a low or absent cytotoxicity, so that these compounds will have little or no side effect in in vivo animal studies. FIG. 8 shows that SID 14730725 and SID 3712502 have little or no cytotoxicity in cultured PC3 and C4-2 cells.

Figure 9A:
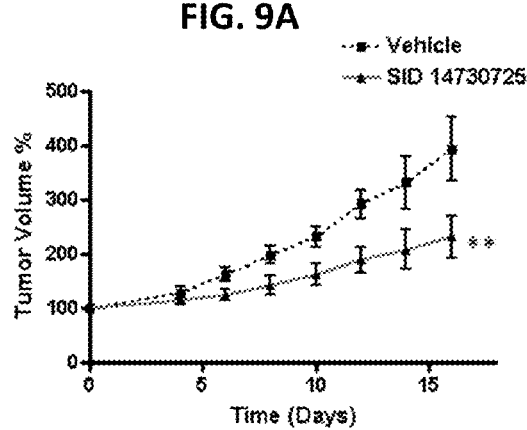
FIGS. 9A and 9B.

SID 14730725 inhibited C4-2 tumor growth in castrated SCID mice. Since SID 14730725 exhibited little or no cytotoxicity while effectively inhibiting AR nuclear localization in C4-2 cells, whether SID 14730725 can inhibit castration-resistant growth of C4-2 xenograft tumors was tested. FIG. 9 shows that SID 14730725 was able to inhibit the growth of a C4-2 xenograft tumor with statistical significance.

Figure 9B:
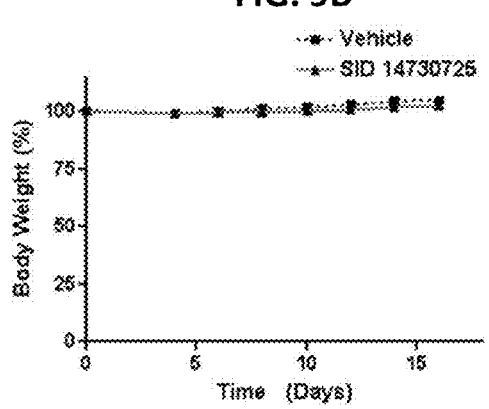

The SID 14730725 did not affect the body weight of injected mice (FIG. 9B), suggesting that this molecule does not have significant toxicity in the mouse model. This observation is in agreement with the predicted LD50 of >300 mg/kg for SID 14730725. The "acute systemic toxicity" (LD50) of the small molecules was calculated using an ADME/Tox predictive model (ACD Labs, Toronto, Canada). The model was developed using data for more than 100,000 compounds. Predictions of LD50 are supported by a reliability estimation (Reliability Index). The LD50 for SID 14730725 is >300 mg/kg in mice using subcutaneous delivery, which is significantly higher than the dosage at ~50 mg/kg used in subcutaneous injection in our preliminary studies (FIG. 9). This in vivo observation argues for a strong potential for SID 14730725 as a pharmaceutical agent that can effectively block AR nuclear localization with little or no side-effect.

The results also indicate that SID 3712502 can cause degradation of endogenous AR in C4-2 and LNCaP cells (FIG. 10), in addition to blocking nuclear localization of AR. This observation suggested that SID 3712502 targets AR differently from SID 14730725. Also, SID 3712502 exhibited little or no cytotoxicity to various cultured cells (FIG. 8). These observations argue that SID 3712502 can serve as another agent for developing therapeutics to target AR in CRPC cells.

The other candidate small molecules identified in the high throughput screen were either highly cytotoxic or did not significantly affect AR localization at 25 uM.

Figure 10A:
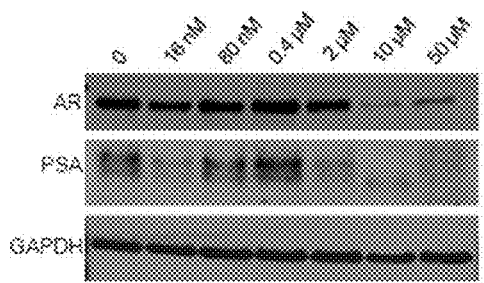
FIGS. 10A and 10B. Down-regulation of the expression of AR and its downstream target PSA by SID 3712502 in C4-2 (FIG. 10A) and LNCaP (FIG. 10B) cells. Cells in RPMI 1640 complete medium were treated with SID 3712502 or vehicle DMSO at the indicated concentrations for 48 hrs. The cells were then harvested in RIPA buffer for Western blot analysis using antibodies for AR, PSA, and GAPDH. GAPDH was included as a loading control.
Figure 10B:
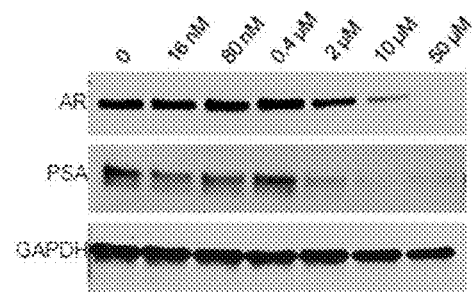

Additional work showed that SID 3712502 can inhibit AR function in C4-2 and 22Rv1 cells (FIG. 10A and FIG. 13A). As expected, AR-target gene PSA expression was significantly inhibited by SID 3712502 at 2 uM. Since 22Rv1 also expresses AR splice variants, SID 3712502 is likely to inhibit AR splice variants as well. Interestingly, SID 3712502 at 10-50 uM also inhibited AR protein levels. Taking the above observations together, SID 3712502 can inhibit AR function at low concentration and AR protein levels at high concentration. The luciferase assay in FIG. 13B and FIG. 13C further demonstrated that SID 3712502 can inhibit the transactivation activity of full-length AR or AR(1-665), which is consistent with the finding that SID 3712502 can inhibit endogenous full-length AR and AR splice variants (FIG. 10A and FIG. 13A).

Further work (FIG. 14) showed that SID 3712502 inhibited the proliferation of AR-positive prostate cancer cells, including C4-2, LNCaP, 22Rv1, and LAPC4, but not AR-negative cell lines PC3 and DU145. SID 3712502 had no detectable effect on AR-negative cells even at 50 uM, the highest concentration in the assay, supporting the conclusion that SID 3712502 specifically targets AR-positive cells.

Figure 15A:
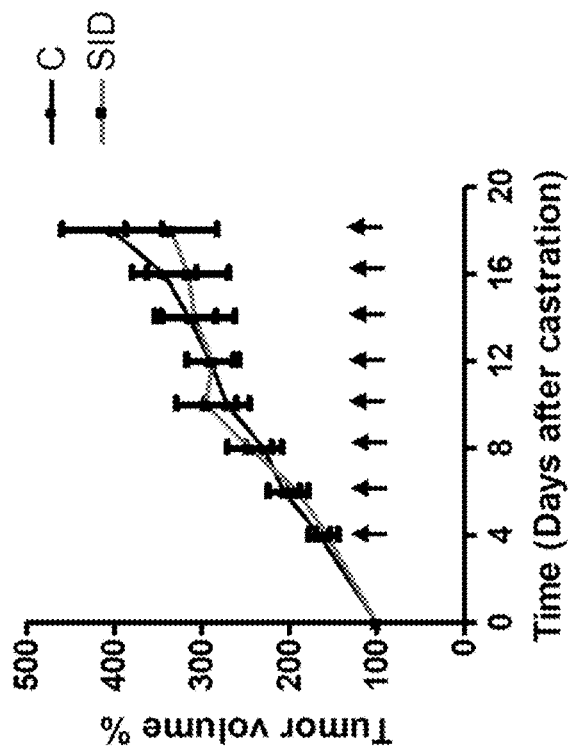
FIGS. 15A-B. SID 3712502 inhibited the growth of castration resistant 22Rv1 xenograft tumors (FIG. 15A), but not PC3 tumors (FIG. 15B). 22Rv1 or PC3 tumors were established by s.c. injection of 1×10⁶ cells into young adult male SCID mice. SCID mice were castrated and randomized when tumor volume reached ~400 uL. Mice received i.p. delivery of SID 3712502 (25 mg/kg body weight) or vehicle control EPL every other day, beginning 4 days after castration (injection indicated by arrows). Each group consisted of 10 mice for 22Rv1, and 8 mice for PC3 tumors. Tumor volumes were measured using micro-calipers and calculated using the formula (length×width²)/2. Black and red lines represent data from the animals treated with vehicle (C) and SID 3712502 (SID), respectively. P value was calculated using a two-way ANOVA with the Bonferrroni correction (GraphPad). Error bars=SEM. **p<0.01.
Figure 15B:
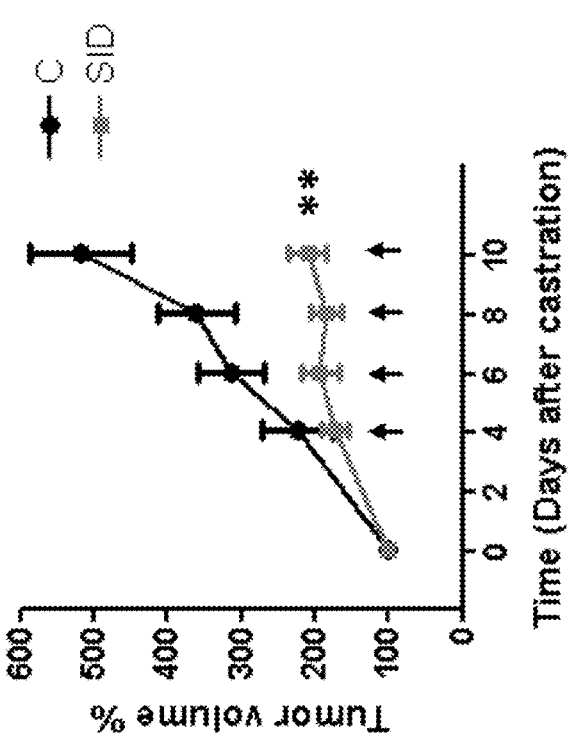

Whether SID 3712502 can inhibit castration-resistant growth of 22Rv1 xenograft tumors was also tested. FIG. 15A shows that i.p. injection of SID 3712502 at 25 mg/kg every other day significantly inhibited the growth of 22Rv1 xenograft tumor (P<0.01). In contrast, SID 3712502 did not inhibit AR-negative PC3 tumor (FIG. 15B). A pilot experiment was also performed testing the toxicity of SID 3712502 in mice. The highest concentration tested was 100 mg/kg, and no identifiable effect on mice was observed at all doses tested (data not shown), indicating a broad therapeutic window for SID 3712502 in the treatment of CRPC.

Certain embodiments are described below in the following numbered paragraphs:

1. A method for treating prostate cancer in a subject, comprising administering a therapeutically effective amount of at least one agent to the subject, wherein the agent is selected from:
    (a) a phenyl-substituted imidazole, or a pharmaceutically acceptable salt of ester thereof; or
    (b) a compound, or a pharmaceutically acceptable salt of ester thereof, having a formula I of:

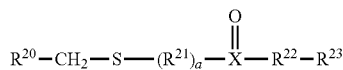

wherein $R^{20}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

$R^{21}$ is an alkanediyl or a substituted alkanediyl;

a is 0 or 1;

X is C or S;

$R^{22}$ is a moiety that includes at least one divalent amino radical; and $R^{23}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group.

2. The method of paragraph 1, wherein the cancer is castration-resistant prostate cancer.

3. The method of paragraph 1 or 2, wherein administration of the agent inhibits androgen receptor nuclear localization in castration-resistant prostate cancer cells.

4. The method of paragraph 1 or 2, wherein administration of the agent inhibits androgen receptor nuclear localization in castration-resistant prostate cancer cells, but does not inhibit glucocorticoid receptor localization and estrogen receptor localization.

5. The method of any one of paragraphs 1 to 4, wherein administration of the agent reduces the nuclear level of androgen receptor in castration-resistant prostate cancer cells relative to untreated control castration-resistant prostate cancer cells.

6. The method of any one of paragraphs 1 to 5, wherein the agent is orally administered.

7. The method of any one of paragraphs 1 to 6, wherein the method is used in combination with androgen deprivation therapy.

8. The method of any one of paragraphs 1 to 6, wherein the agent is co-administered with abiratrone.

9. The method of any one of paragraphs 1 to 8, wherein the method further comprises identifying a subject that is in need of treatment with the agent.

10. The method of any one of paragraphs 1 to 9, wherein the agent comprises a phenyl-substituted imidazole.

11. The method of paragraph 10, wherein the phenyl-substituted imidazole is a phenyl-substituted pyrroloimidazole.

12. The method of paragraph 11, wherein the phenyl-substituted pyrroloimidazole includes a 6,7-dihydro-5H-pyrrolo[1,2-a]imidazole moiety.

13. The method of paragraph 12, wherein the phenyl group is substituted at the 3 position of the 6,7-dihydro-5H-pyrrolo[1,2-a]imidazole moiety.

14. The method of any one of paragraphs 1 to 13, wherein the phenyl of the phenyl-substituted imidazole includes at least one substituent.

15. The method of paragraph 14, wherein the phenyl substituent is located at the para position relative to the position of the phenyl-pyrroloimidazole bond.

16. The method of paragraph 14 or 15, wherein the phenyl substituent is selected from halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group.

17. The method of paragraph 10, wherein the phenyl-substituted imidazole has a structure of formula II:

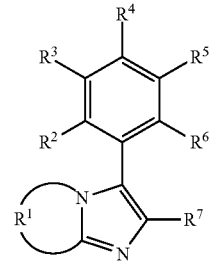

wherein $R^1$ forms a ring structure selected from an optionally substituted single ring that includes four to six C ring atoms, or an optionally substituted polycyclic ring that includes five to ten C ring atoms;

$R^2$ to $R^6$ is each individually H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group; and $R^7$ is H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group.

18. The method of paragraph 17, wherein $R^1$ forms a ring structure that includes four C ring atoms; $R^2$, $R^3$, $R^5$ and $R^6$ are each individually H; $R^4$ is halogen, alkoxy, aryl, substituted aryl, heteroaryl, alkyl, or substituted alkyl; and $R^7$ is H.

19. The method of paragraph 17, wherein the agent is selected from:

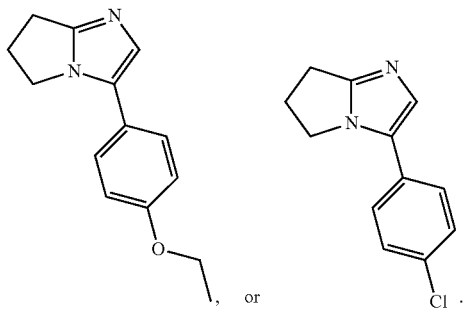 [SMILES: CCOc1ccc(-c2cnc3n2CCC3)cc1 ; Clc1ccc(-c2cnc3n2CCC3)cc1]

20. The method of any one of paragraphs 1 to 9, wherein the agent comprises a compound of formula I.

21. The method of paragraph 20, wherein the agent is:

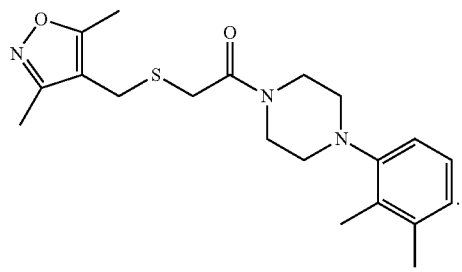 [SMILES: Cc1cccc(N2CCN(C(=O)CSCc3c(C)noc3C)CC2)c1C]

22. A compound, or a pharmaceutically acceptable salt or ester thereof, having a structure of formula II:

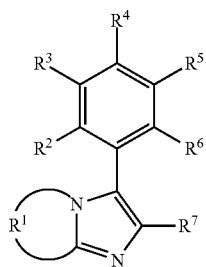

wherein $R^1$ forms a ring structure selected from an optionally substituted single ring that includes four to six C ring atoms, or an optionally substituted polycyclic ring that includes five to ten C ring atoms;

$R^2$ to $R^6$ is each individually H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group; and $R^7$ is H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group, with the proviso that the compound of formula II is not:

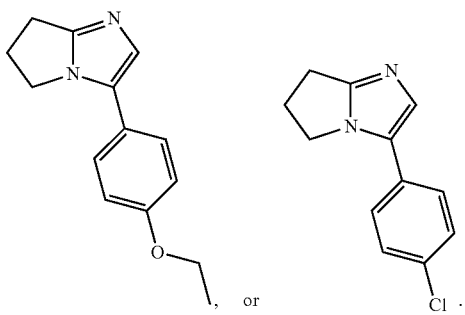 [SMILES: CCOc1ccc(-c2cnc3n2CCC3)cc1 ; Clc1ccc(-c2cnc3n2CCC3)cc1]

23. The compound of paragraph 20, wherein $R^1$ forms a ring structure that includes four C ring atoms; $R^2$, $R^3$, $R^5$ and $R^6$ are each individually H; $R^4$ is halogen, alkoxy, aryl, substituted aryl, heteroaryl, alkyl, or substituted alkyl; and $R^7$ is H.

24. A compound, or a pharmaceutically acceptable salt or ester thereof, having a structure of formula I:

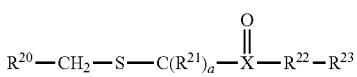

wherein $R^{20}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group;

$R^{21}$ is an alkanediyl or a substituted alkanediyl;

a is 0 or 1;

X is C or S;

$R^{22}$ is a moiety that includes at least one divalent amino radical; and $R^{23}$ is an aryl, substituted aryl, heteroaryl, substituted heteroaryl, heterocycloalkyl, substituted heterocycloalkyl, alkoxy, aryloxy, a silyl-containing group, a boryl-containing group, a phosphine-containing group, amino, a thio-containing group, a seleno-containing group, halide, or a nitro-containing group, with the proviso that the compound of formula I is not:

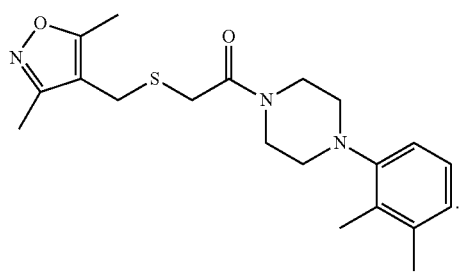 [SMILES: Cc1cccc(N2CCN(C(=O)CSCc3c(C)noc3C)CC2)c1C]

25. A pharmaceutical composition comprising at least one pharmaceutically acceptable additive, and a compound of paragraph 22 or 23.

26. A pharmaceutical composition comprising at least one pharmaceutically acceptable additive, and a compound of paragraph 24.

In view of the many possible embodiments to which the principles of the disclosed invention may be applied, it should be recognized that the illustrated embodiments are only preferred examples of the invention and should not be taken as limiting the scope of the invention.

What is claimed is:

1. A compound, or a pharmaceutically acceptable salt or ester thereof, of a structure of:

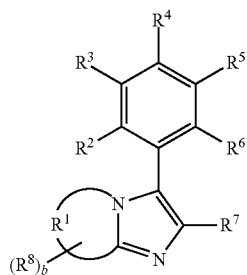

wherein $R^1$ forms a ring structure selected from an optionally substituted single ring that includes four to six C ring atoms, or an optionally substituted polycyclic ring that includes five to ten C ring atoms;

$R^2$ to $R^6$ is each individually H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group;

$R^7$ is H, halogen, alkoxy, aryl, heteroaryl, alkyl, substituted alkyl, aryloxy, a silyl-containing group, a boryl-containing group, a phosphine-containing group, amino, a thio-containing group, a seleno-containing group, or a nitro-containing group;

$R^8$ is hydroxy, alkoxy, hydroxyalkyl, or alkoxyalkyl; and b is 1.

2. A compound, or a pharmaceutically acceptable salt or ester thereof, of a structure of:

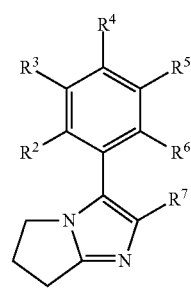

wherein $R^2$, $R^3$, $R^5$, $R^6$ and $R^7$ are each individually H; and $R^4$ is substituted aryl, heteroaryl, alkyl, substituted alkyl, aryloxy, a silyl-containing group, a boryl-containing group, a phosphine-containing group, amino, a thio-containing group, or a seleno-containing group.

3. A compound, or a pharmaceutically acceptable salt or ester thereof, of a structure of:

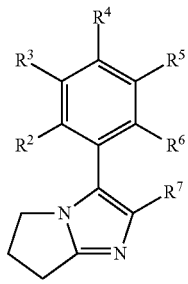

$R^2$ to $R^6$ is each individually H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containin group; and $R^7$ is halogen, alkoxy, aryl, alkyl, substituted alkyl, aryloxy, a silyl-containing group, a boryl-containing group, a phosphine-containing group, amino, a thio-containing group, a seleno-containing group, or a nitro-containing group.

4. A compound, or a pharmaceutically acceptable salt or ester thereof, of a structure of:

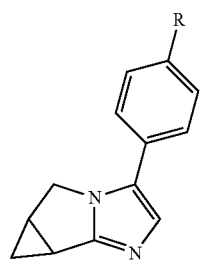

wherein R is alkoxy or halogen.

5. A compound, or a pharmaceutically acceptable salt or ester thereof, of a structure of:

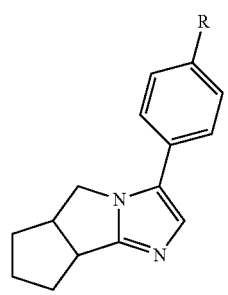

wherein R is alkoxy or halogen.

6. A compound, or a pharmaceutically acceptable salt or ester thereof, of a structure of:

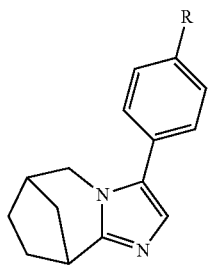

wherein R is alkoxy or halogen.

7. A compound, or a pharmaceutically acceptable salt or ester thereof, of a structure of:

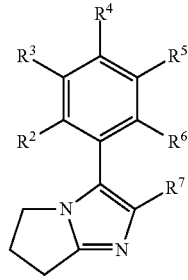

wherein $R^4$ is H;

at least one of $R^2$, $R^3$, $R^5$ or $R^6$ is halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group; and $R^7$ is H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group.

8. The compound of claim 7, wherein $R^5$ or $R^6$ is halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group.

9. A pharmaceutical composition comprising at least one pharmaceutically acceptable additive, and a compound of claim 1.

10. A pharmaceutical composition comprising at least one pharmaceutically acceptable additive, and a compound of claim 2.

11. A pharmaceutical composition comprising at least one pharmaceutically acceptable additive, and a compound of claim 3.

12. A pharmaceutical composition comprising at least one pharmaceutically acceptable additive, and a compound of claim 4.

13. A pharmaceutical composition comprising at least one pharmaceutically acceptable additive, and a compound of claim 5.

14. A pharmaceutical composition comprising at least one pharmaceutically acceptable additive, and a compound of claim 6.

15. A pharmaceutical composition comprising at least one pharmaceutically acceptable additive, and a compound of claim 7.

16. The compound of claim 1, wherein $R^4$ is halogen or $C_1$-$C_8$ alkoxy.

17. The compound of claim 1, wherein $R^8$ is hydroxy.

18. The compound of claim 17, wherein $R^4$ is $C_1$-$C_8$ alkoxy.

19. A compound, or a pharmaceutically acceptable salt or ester thereof, of a structure of:

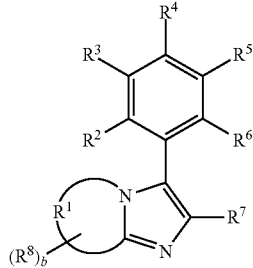

wherein $R^1$ forms a ring structure selected from an optionally substituted single ring that includes four to six C ring atoms, or an optionally substituted polycyclic ring that includes five to ten C ring atoms;

$R^2$ to $R^6$ is each individually H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group;

$R^7$ is H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group;

$R^8$ is alkoxy, hydroxyalkyl, or alkoxyalkyl; and b is 1.

20. A compound, or a pharmaceutically acceptable salt or ester thereof, of a structure of:

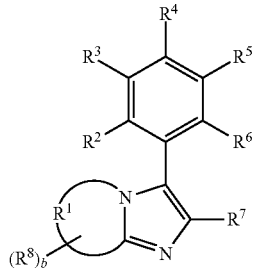

wherein $R^1$ forms a ring structure selected from an optionally substituted single ring that includes four to six C ring atoms, or an optionally substituted polycyclic ring that includes five to ten C ring atoms;

$R^2$ to $R^6$ is each individually H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group;

$R^7$ is 2-chlorothiophene;
$R^8$ is hydroxy, alkoxy, hydroxyalkyl, or alkoxyalkyl; and
b is 1.

21. A compound, or a pharmaceutically acceptable salt or ester thereof, of a structure of:

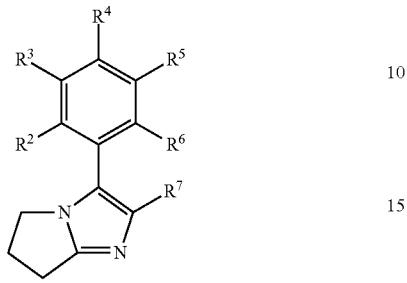

$R^2$ to $R^6$ is each individually H, halogen, alkoxy, aryl, substituted aryl, heteroaryl, alkyl, substituted alkyl, aryloxy, a silyl-containing group, a boryl-containing group, a phosphine-containing group, amino, a thio-containing group, a seleno-containing group, or a nitro-containing group; and
$R^7$ is 2-chlorothiophene.

* * * * *